(12) United States Patent
Majima et al.

(10) Patent No.: US 7,865,012 B2
(45) Date of Patent: Jan. 4, 2011

(54) SEMICONDUCTOR FAILURE ANALYSIS APPARATUS WHICH ACQUIRES A FAILURE OBSERVED IMAGE, FAILURE ANALYSIS METHOD, AND FAILURE ANALYSIS PROGRAM

(75) Inventors: Toshiyuki Majima, Kodaira (JP); Akira Shimase, Kodaira (JP); Hirotoshi Terada, Hamamatsu (JP); Kazuhiro Hotta, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 1057 days.

(21) Appl. No.: 11/586,721

(22) Filed: Oct. 26, 2006

(65) Prior Publication Data

US 2007/0292018 A1 Dec. 20, 2007

(30) Foreign Application Priority Data

Jun. 14, 2006 (JP) ............................ P2006-165204

(51) Int. Cl.
*G06K 9/00* (2006.01)
(52) U.S. Cl. .................... 382/149; 382/150; 382/147; 382/145
(58) Field of Classification Search ................. 382/144, 382/149, 152
See application file for complete search history.

(56) References Cited

U.S. PATENT DOCUMENTS

| | | | |
|---|---|---|---|
| 5,240,866 A | 8/1993 | Friedman et al. | |
| 5,930,382 A * | 7/1999 | Irie et al. | 382/147 |
| 6,292,582 B1 | 9/2001 | Lin et al. | |
| 6,553,546 B1 | 4/2003 | Murakami | |
| 6,775,817 B2 | 8/2004 | Ono et al. | |
| 6,891,363 B2 | 5/2005 | Desplats et al. | |
| 7,079,971 B2 | 7/2006 | Fukuda | |
| 2001/0000460 A1 | 4/2001 | Ishihara et al. | |
| 2002/0024603 A1 | 2/2002 | Nakayama et al. | |
| 2002/0060650 A1 | 5/2002 | Wakashiro et al. | |
| 2002/0144219 A1 | 10/2002 | Zachariah et al. | |
| 2003/0174877 A1 | 9/2003 | Aiger | |
| 2004/0107412 A1 | 6/2004 | Pack et al. | |

(Continued)

FOREIGN PATENT DOCUMENTS

CN  1444035  9/2003

(Continued)

*Primary Examiner*—Brian Q Le
*Assistant Examiner*—Edward Park
(74) *Attorney, Agent, or Firm*—Drinker Biddle & Reath LLP

(57) ABSTRACT

A failure analysis apparatus 10 is composed of an inspection information acquirer 11 for acquiring a failure observed image P2 of a semiconductor device, a layout information acquirer 12 for acquiring layout information, and a failure analyzer 13 for analyzing a failure. The failure analyzer 13 extracts as a candidate interconnection for a failure, an interconnection passing an analysis region, out of a plurality of interconnections, using interconnection information to describe a configuration of interconnections in the semiconductor device by a pattern data group of interconnection patterns in respective layers, and, for extracting the candidate interconnection, it performs an equipotential trace of the interconnection patterns using the pattern data group, thereby extracting the candidate interconnection. This substantializes a semiconductor failure analysis apparatus, failure analysis method, and failure analysis program capable of securely and efficiently performing the analysis of the failure of the semiconductor device using the failure observed image.

18 Claims, 19 Drawing Sheets

U.S. PATENT DOCUMENTS

| | | |
|---|---|---|
| 2004/0139407 A1 | 7/2004 | Mukai et al. |
| 2004/0208353 A1 | 10/2004 | Murakami |
| 2004/0243891 A1 | 12/2004 | Ohta |
| 2005/0076316 A1 | 4/2005 | Pierrat et al. |
| 2005/0147287 A1 | 7/2005 | Sakai et al. |
| 2005/0231219 A1 | 10/2005 | Desplats et al. |
| 2006/0098862 A1 | 5/2006 | Demarest et al. |
| 2006/0215901 A1* | 9/2006 | Nakagaki et al. ............ 382/149 |
| 2007/0230770 A1 | 10/2007 | Kulkarni et al. |

FOREIGN PATENT DOCUMENTS

| | | |
|---|---|---|
| JP | 4-138574 | 5/1992 |
| JP | 5-181924 | 7/1993 |
| JP | 8-250560 | 9/1996 |
| JP | 10-004128 | 1/1998 |
| JP | 10-063235 | 3/1998 |
| JP | 11-16974 | 1/1999 |
| JP | 2001-201545 | 7/2001 |
| JP | 2001-203248 | 7/2001 |
| JP | 2003-86689 | 3/2003 |
| JP | 2003-282665 | 10/2003 |
| JP | 2003-303746 | 10/2003 |
| JP | 3519872 | 2/2004 |

* cited by examiner

Fig.3
(a)
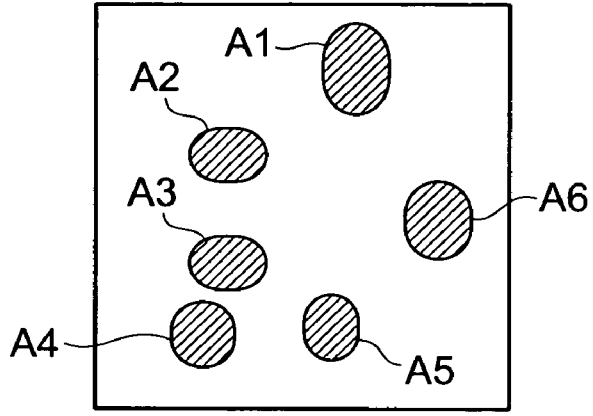
(b)
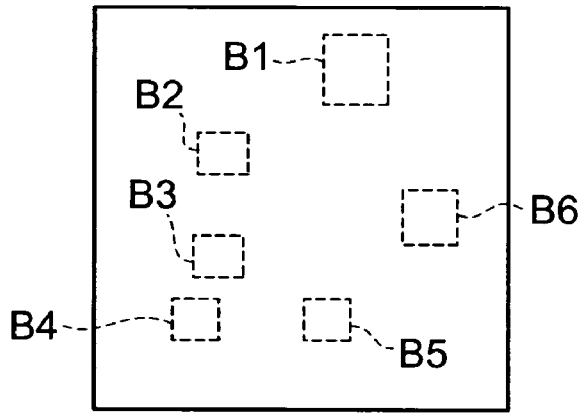
(c)
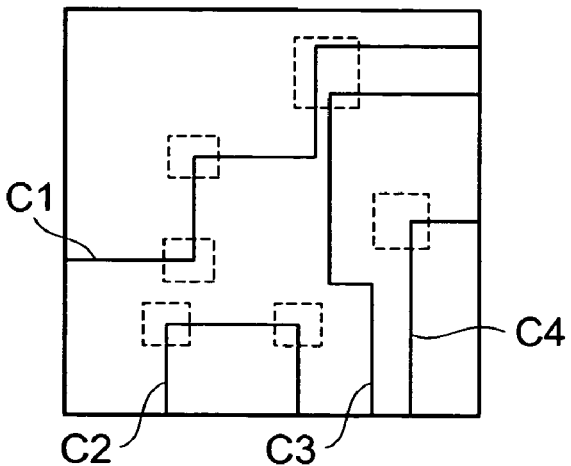

Fig.4
(a)
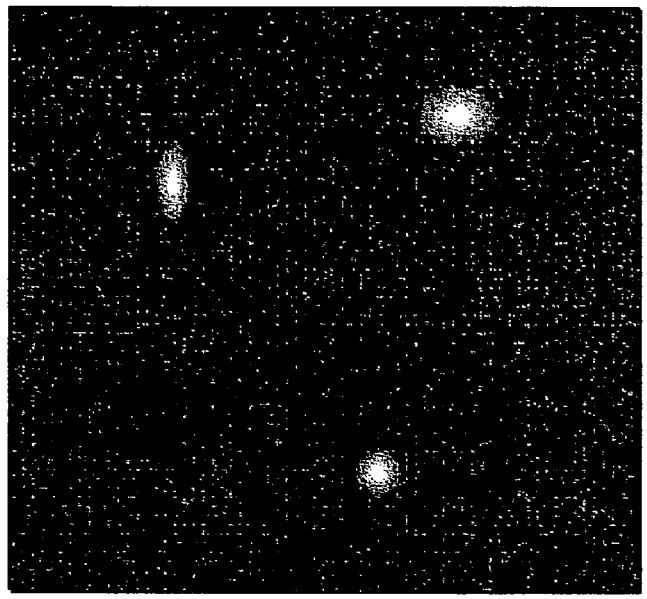
(b)
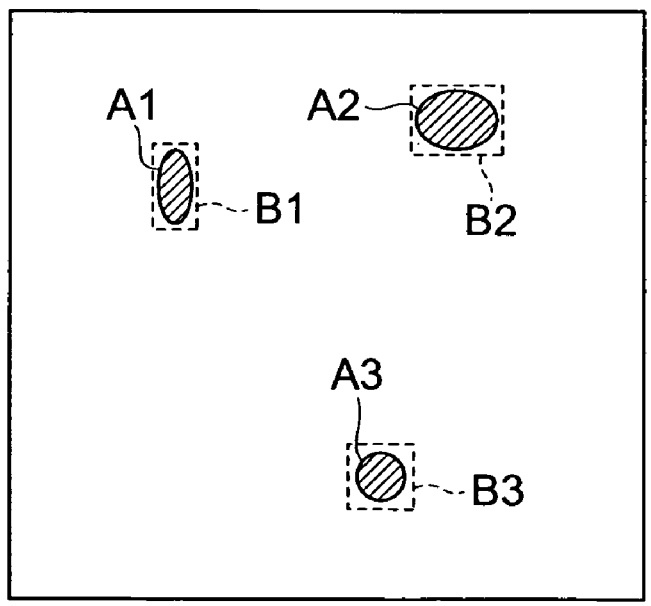

Fig.6
(a)
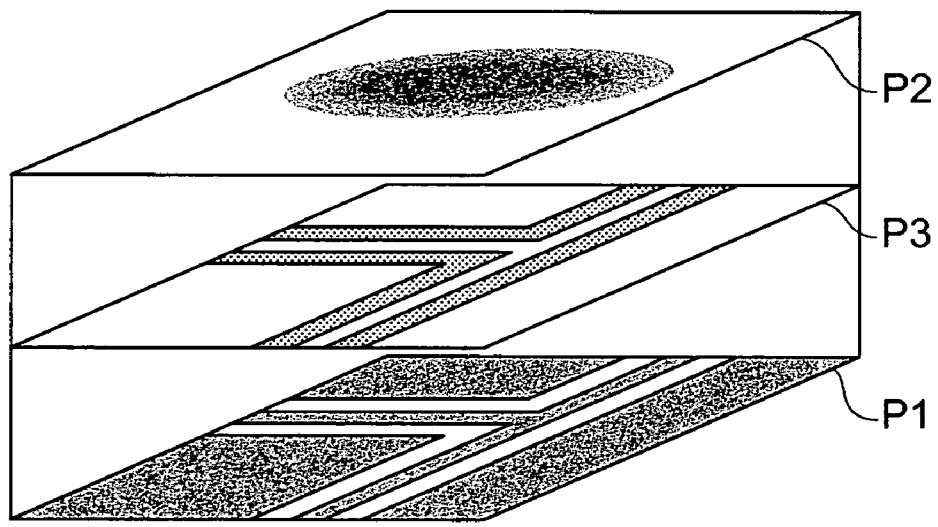
(b)
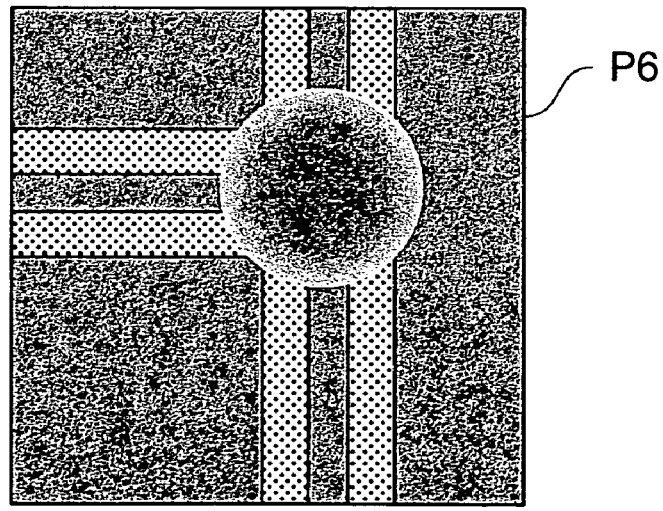

Fig.18
(a)
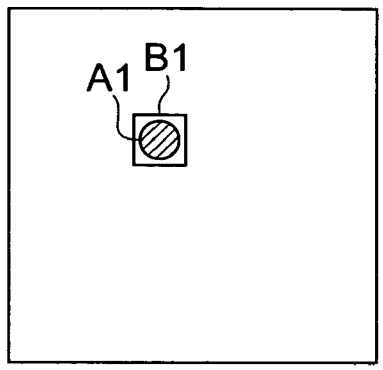
(d)
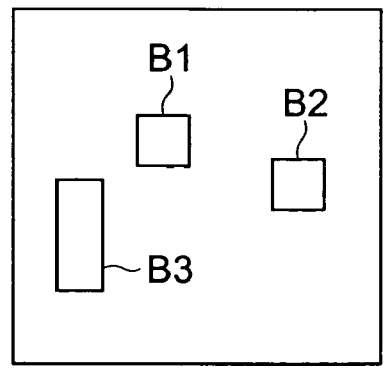
(b)
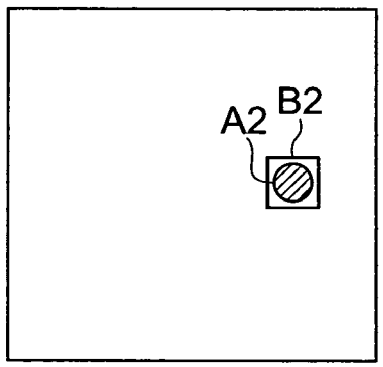
(e)
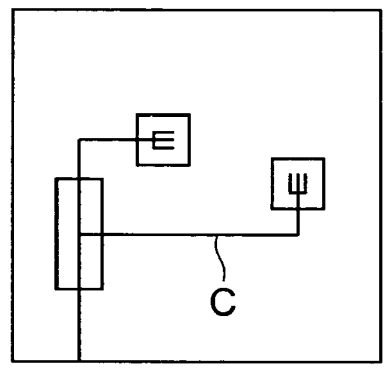
(c)
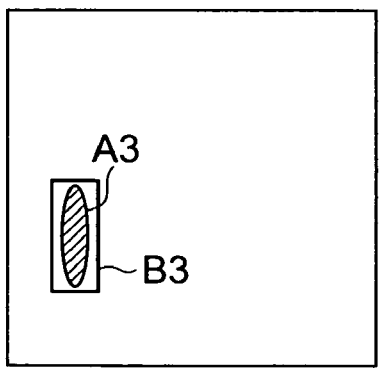

SEMICONDUCTOR FAILURE ANALYSIS APPARATUS WHICH ACQUIRES A FAILURE OBSERVED IMAGE, FAILURE ANALYSIS METHOD, AND FAILURE ANALYSIS PROGRAM

BACKGROUND OF THE INVENTION

1. Field of the Invention

The present invention relates to a semiconductor failure analysis apparatus, failure analysis method, and failure analysis program for analyzing a failure of a semiconductor device.

2. Related Background Art

The conventionally available semiconductor inspection apparatus for acquiring an observed image for analysis of failure of a semiconductor device include emission microscopes, OBIRCH apparatus, time-resolved emission microscopes, and so on. These inspection apparatus are able to analyze such a failure as a broken part in a semiconductor device by use of an emission image or OBIRCH image acquired as a failure observed image (e.g., reference is made to Patent Document 1: Japanese Patent Application Laid-Open No. 2003-86689 and to Patent Document 2: Japanese Patent Application Laid-Open No. 2003-303746).

SUMMARY OF THE INVENTION

In recent years, semiconductor devices as analysis objects in the semiconductor failure analysis have been miniaturized and integrated more and more, and it has become difficult to perform the analysis of failure part by means of the aforementioned inspection apparatus. In order to analyze the failure part of such a semiconductor device, it is thus essential to improve certainty and efficiency of the analysis process for estimating the failure part of the semiconductor device from the failure observed image.

The present invention has been accomplished in order to solve the above problem, and an object of the invention is to provide a semiconductor failure analysis apparatus, failure analysis method, and failure analysis program capable of securely and efficiently performing an analysis of a failure of a semiconductor device with use of a failure observed image.

In order to achieve the above object, a semiconductor failure analysis apparatus according to the present invention is a semiconductor failure analysis apparatus for analyzing a failure of a semiconductor device, comprising: (1) inspection information acquiring means for acquiring a failure observed image containing reaction information arising from a failure, acquired by conducting an inspection about the failure, as an observed image of the semiconductor device; (2) layout information acquiring means for acquiring layout information of the semiconductor device; and (3) failure analyzing means for analyzing the failure of the semiconductor device with reference to the failure observed image and the layout information; (4) wherein the failure analyzing means has region setting means for setting an analysis region in correspondence to the reaction information with reference to the failure observed image, and interconnection information analyzing means for performing an analysis of a failure in a plurality of interconnections included in a layout of the semiconductor device, with reference to the analysis region; (5) wherein the layout information contains interconnection information to describe a configuration of the plurality of interconnections in the semiconductor device by a pattern data group of interconnection patterns in respective layers in a layer structure of the semiconductor device; and (6) wherein the interconnection information analyzing means extracts an interconnection passing the analysis region out of the plurality of interconnections, as a candidate interconnection for a failure and, for extracting the candidate interconnection, the interconnection information analyzing means performs an equipotential trace of the interconnection patterns using the pattern data group, thereby extracting the candidate interconnection.

A semiconductor failure analysis method according to the present invention is a semiconductor failure analysis method of analyzing a failure of a semiconductor device, comprising: (1) an inspection information acquiring step of acquiring a failure observed image containing reaction information arising from a failure, acquired by conducting an inspection about the failure, as an observed image of the semiconductor device; (2) a layout information acquiring step of acquiring layout information of the semiconductor device; and (3) a failure analyzing step of analyzing the failure of the semiconductor device with reference to the failure observed image and the layout information; (4) wherein the failure analyzing step comprises a region setting step for setting an analysis region in correspondence to the reaction information with reference to the failure observed image, and an interconnection information analyzing step of performing an analysis of a failure in a plurality of interconnections included in a layout of the semiconductor device, with reference to the analysis region; (5) wherein the layout information contains interconnection information to describe a configuration of the plurality of interconnections in the semiconductor device by a pattern data group of interconnection patterns in respective layers in a layer structure of the semiconductor device; and (6) wherein the interconnection information analyzing step comprises extracting an interconnection passing the analysis region out of the plurality of interconnections, as a candidate interconnection for a failure and, for extracting the candidate interconnection, the interconnection information analyzing step comprises performing an equipotential trace of the interconnection patterns using the pattern data group, thereby extracting the candidate interconnection.

A semiconductor failure analysis program according to the present invention is a program for letting a computer execute a semiconductor failure analysis of analyzing a failure of a semiconductor device, the program letting the computer execute: (1) an inspection information acquiring process of acquiring a failure observed image containing reaction information arising from a failure, acquired by conducting an inspection about the failure, as an observed image of the semiconductor device; (2) a layout information acquiring process of acquiring layout information of the semiconductor device; and (3) a failure analyzing process of analyzing the failure of the semiconductor device with reference to the failure observed image and the layout information; (4) wherein the failure analyzing process comprises a region setting process for setting an analysis region in correspondence to the reaction information with reference to the failure observed image, and an interconnection information analyzing process of performing an analysis of a failure in a plurality of interconnections included in a layout of the semiconductor device, with reference to the analysis region; (5) wherein the layout information contains interconnection information to describe a configuration of the plurality of interconnections in the semiconductor device by a pattern data group of interconnection patterns in respective layers in a layer structure of the semiconductor device; and (6) wherein the interconnection information analyzing process comprises extracting an interconnection passing the analysis region out of the plurality of interconnections, as a candidate interconnection for a failure and, for extracting the candidate interconnection, the interconnection information analyzing process comprises performing an equipotential trace of the interconnection patterns using the pattern data group, thereby extracting the candidate interconnection.

The above-described semiconductor failure analysis apparatus, failure analysis method, and failure analysis program are arranged to acquire the failure observed image such as an emission image or OBIRCH image acquired by conducting an inspection of the semiconductor device as an analysis object, and necessary information about the layout of the semiconductor device. Then the analysis region is set in correspondence to the reaction information (e.g., information about a reaction part) in the failure observation image, and an interconnection passing the analysis region is extracted out of the interconnections (nets) constituting the semiconductor device, thereby performing the analysis of the failure of the semiconductor device. This configuration permits us to estimate a candidate interconnection with a high possibility of a failure in the semiconductor device by suitably setting the analysis region and extracting an interconnection passing the analysis region.

Furthermore, the above configuration uses the interconnection information to describe the configuration of the plurality of interconnections by the pattern data group being an aggregate of interconnection patterns in the respective layers in the layer structure, as data indicating the interconnection configuration in the semiconductor device. For extracting a candidate interconnection for a failure, the equipotential trace of the interconnection patterns is carried out in the pattern data group to extract a candidate interconnection (candidate net). This configuration permits us to efficiently execute the extraction of the candidate interconnection for the failure, using the interconnection information, for example, the GDS data or the like relatively easy to acquire. Therefore, it becomes feasible to securely and efficiently perform the failure analysis of the semiconductor device using the failure observed image.

Since the semiconductor failure analysis apparatus, failure analysis method, and failure analysis program according to the present invention are arranged to extract an interconnection passing the analysis region set in the failure observed image, as a candidate interconnection for a failure, to use the interconnection information to describe the configuration of the plurality of interconnections by the pattern data group of interconnection patterns in the respective layers in the layer structure of the semiconductor device, and, in extraction of the candidate interconnection, to perform the equipotential trace of the interconnection patterns using the pattern data group to extract the candidate interconnection, they permit us to efficiently execute the extraction of the candidate interconnection using the interconnection information and to securely and efficiently perform the failure analysis of the semiconductor device.

BRIEF DESCRIPTION OF THE DRAWINGS

FIG. 3 is a drawing schematically showing a semiconductor failure analysis method.

FIG. 4 is a drawing schematically showing extraction of reaction regions and setting of analysis regions.

FIG. 6 is a drawing schematically showing a correspondence among observed images and a layout image.

FIG. 18 is a drawing schematically showing an example of an analysis process using a failure observed image.

DESCRIPTION OF THE PREFERRED EMBODIMENTS

Figure 1:
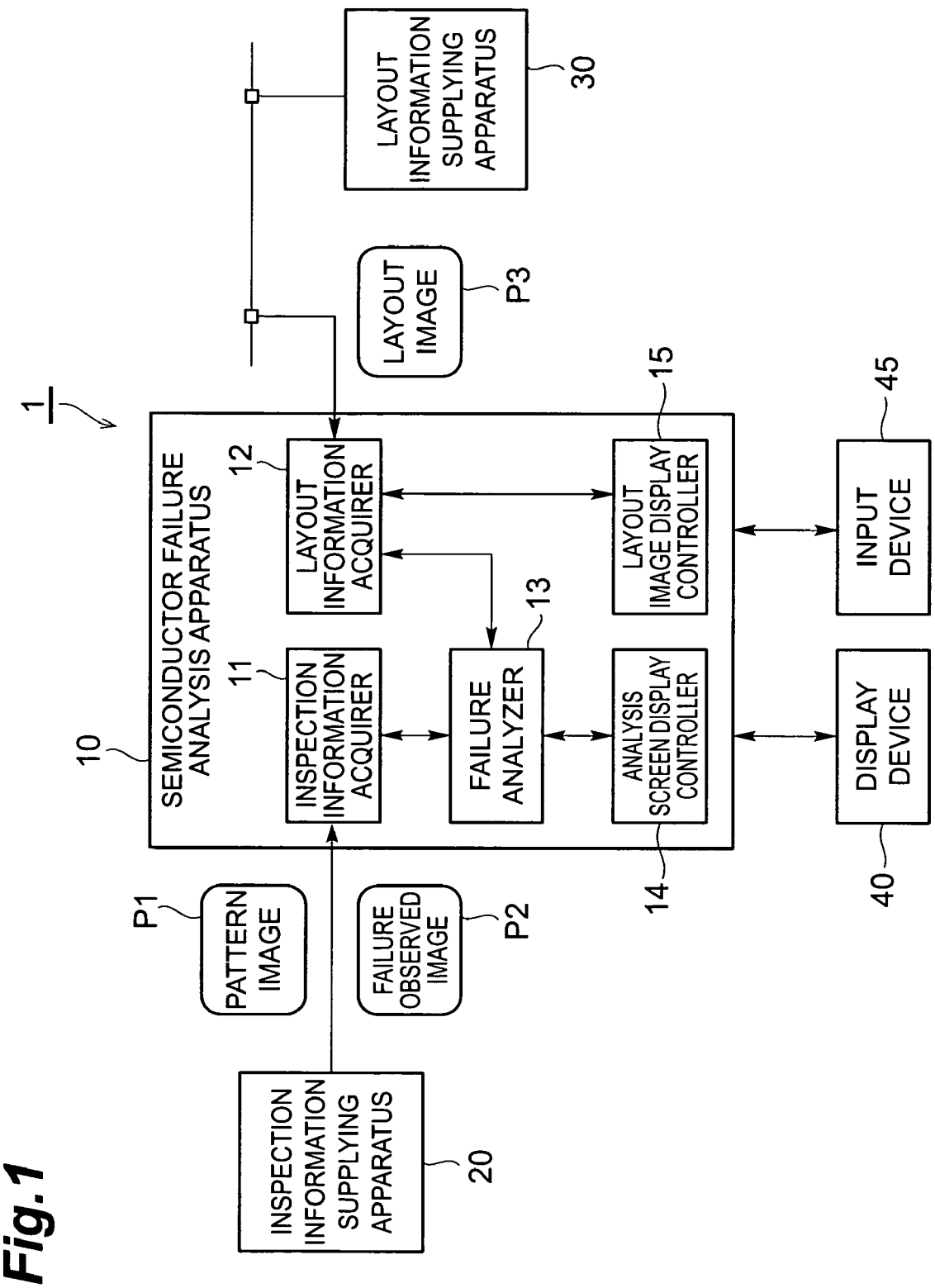
FIG. 1 is a block diagram showing a configuration of an embodiment of a failure analysis system incorporating the semiconductor failure analysis apparatus.

Preferred embodiments of the semiconductor failure analysis apparatus, failure analysis method, and failure analysis program according to the present invention will be described below in detail with reference to the drawings. In the description of the drawings the same elements will be denoted by the same reference symbols, without redundant description. It is also noted that dimensional ratios in the drawings do not always agree with those in the description.

FIG. 1 is a block diagram schematically showing a configuration of an embodiment of the failure analysis system incorporating the semiconductor failure analysis apparatus according to the present invention. The present failure analysis system 1 is a system an analysis object of which is a semiconductor device and which is for carrying out an analysis of a failure with the use of an observed image thereof, and the system comprises a semiconductor failure analysis apparatus 10, an inspection information supplying apparatus 20, a layout information supplying apparatus 30, a display device 40, and an input device 45. Configurations of the semiconductor failure analysis apparatus 10 and failure analysis system 1 will be described below along with a semiconductor failure analysis method.

The semiconductor failure analysis apparatus 10 is an analyzer for importing data necessary for the analysis of the failure of the semiconductor device and executing the analysis processing of the failure. The failure analysis apparatus 10 according to the present embodiment has an inspection information acquirer 11, a layout information acquirer 12, a failure analyzer 13, an analysis screen display controller 14, and a layout image display controller 15. Devices connected to the failure analysis apparatus 10 include the display device 40 for displaying information about the failure analysis, and the input device 45 used for input of instructions and information necessary for the failure analysis.

Data to be used in the failure analysis executed in the failure analysis apparatus 10 is acquired by the inspection information acquirer 11 and by the layout information acquirer 12. The inspection information acquirer 11 acquires a pattern image P1 being a normal observed image, and a failure observed image P2 containing reaction information arising from a failure, obtained by conducting an inspection about the failure, as observation images of the semiconductor device (inspection information acquiring step). The layout information acquirer 12 acquires layout information indicating a configuration of interconnections or the like in the semiconductor device (layout information acquiring step). In FIG. 1, the layout information acquirer 12 acquires a layout image P3 as the layout information of the semiconductor device.

In FIG. 1, the inspection information supplying apparatus 20 is connected to the inspection information acquirer 11, and the pattern image P1 and the failure observed image P2 are supplied from the supplying apparatus 20 to the acquirer 11. This inspection information supplying apparatus 20 can be, for example, an emission microscope apparatus. In this case, the failure observed image P2 is an emission image. The inspection information supplying apparatus 20 can also be an OBIRCH apparatus. In this case, the failure observed image P2 is an OBIRCH image. Furthermore, the supplying apparatus 20 may also be any other type of semiconductor inspection apparatus than those.

Where the pattern image P1 and the failure observed image P2 are those preliminarily acquired by the semiconductor inspection apparatus, the inspection information supplying apparatus 20 is a data storage device storing those image data. The data storage device in this case may be one provided inside the failure analysis apparatus 10, or an external device. This configuration is useful in a case where observed images are taken and stored in advance by the semiconductor inspection apparatus and where software of failure analysis apparatus 10 is executed on another computer. In this case, works of the failure analysis can be performed as shared, without occupying the semiconductor inspection apparatus.

The pattern image P1 and the failure observed image P2 acquired by the semiconductor inspection apparatus such as the emission microscope apparatus or OBIRCH apparatus are acquired as images P1, P2 in a state in which the semiconductor device is mounted on a stage. For this reason, they are acquired as images aligned relative to each other. The coordinate system on the image in the images P1, P2 is set, for example, corresponding to the stage coordinate system in the semiconductor inspection apparatus.

On the other hand, the layout information supplying apparatus 30 is connected through a network to the layout information acquirer 12, and the layout image P3 is supplied from the supplying apparatus 30 to the acquirer 12. This layout information supplying apparatus 30 can be, for example, a workstation on which a CAD software application of a layout viewer to generate the layout image P3 from design information such as arrangement of elements and nets (interconnections) constituting the semiconductor device, is running.

The failure analysis apparatus 10 is preferably configured to acquire the layout information other than the layout image P3, e.g., individual information of a plurality of nets contained in the semiconductor device, by performing communication with the layout information supplying apparatus 30 as occasion may demand. Alternatively, the failure analysis apparatus 10 may also be configured to retrieve the information together with the layout image P3 from the layout information acquirer 12.

In the layout information supplying apparatus 30, the information of the interconnection configuration of the semiconductor device contained in the layout information is prepared, for example, as data of the GDSII format. The GDSII data is interconnection information to describe a configuration of a plurality of interconnections in a semiconductor device by a pattern data group of interconnection patterns in respective layers in a layer structure of the semiconductor device, and is commonly used in the semiconductor fields. In the GDSII data, specifically, the aforementioned interconnection patterns are expressed by rectangular patterns each of which is specified by a combination of data of a start point, an end point, and a width.

In the present embodiment the failure analysis apparatus 10 is provided with the layout image display controller 15. This layout image display controller 15 is comprised of screen transfer software, e.g., an X terminal, and has a function of displaying the layout image P3 drawn by the layout information supplying apparatus 30, in a predetermined display window in the display device 40. However, the layout image display controller 15 of this configuration does not always have to be provided if it is not necessary.

The pattern image P1, failure observed image P2, and layout image P3 acquired by the inspection information acquirer 11 and by the layout information acquirer 12 are fed to the failure analyzer 13. The failure analyzer 13 is an analyzing means for analyzing a failure of the semiconductor device with reference to the failure observed image P2 and the layout information. The analysis screen display controller 14 is an information display controlling means for letting the display device 40 display the information about the analysis result of the failure of the semiconductor device obtained by the failure analyzer 13. The analysis screen display controller 14 displays the information about the analysis of the failure of the semiconductor device except for the analysis result in a predetermined analysis screen according to need.

Figure 2:
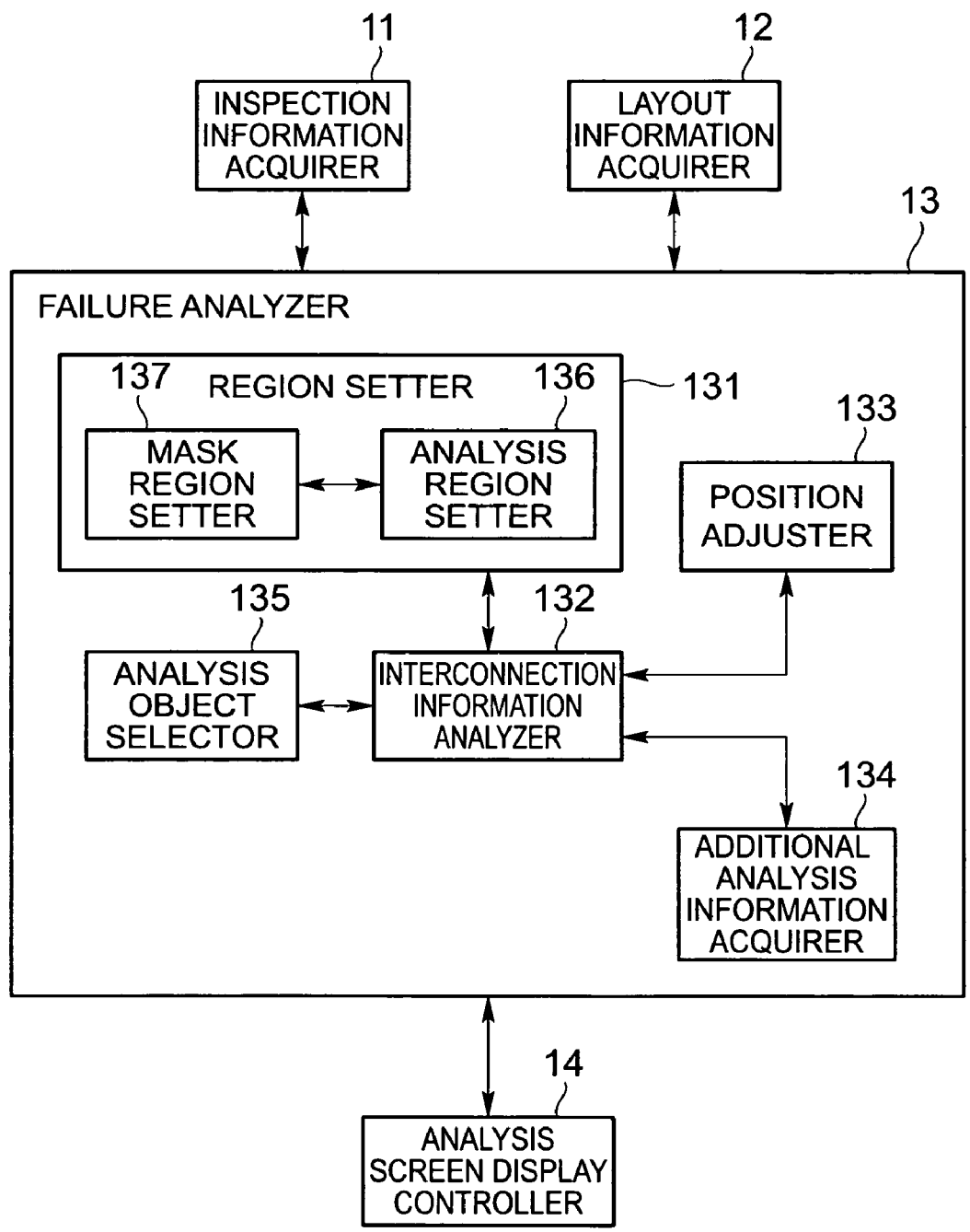
FIG. 2 is a block diagram showing a specific configuration of a failure analyzer.

FIG. 2 is a block diagram showing a specific configuration of the failure analyzer 13 in the semiconductor failure analysis apparatus 10 shown in FIG. 1. The failure analyzer 13 of the present embodiment has a region setter 131 and an interconnection information analyzer 132. FIGS. 3 and 4 are drawings schematically showing a failure analysis method executed by the region setter 131 and the interconnection information analyzer 132. Hereinafter, where the failure observed image and others are schematically illustrated, reaction regions, for example, such as emission regions in an emission image will be illustrated as hatched regions, for description's sake.

The region setter 131 is a setting means for setting an analysis region in correspondence to reaction information in the image P2, with reference to the failure observed image P2, for the semiconductor device as an analysis object. Let us consider an emission image acquired by an emission microscope apparatus, as an example of the failure observed image P2. For example, in an example shown in (a) in FIG. 3, six emission regions A1-A6 (reaction regions) exist as the reaction information referenced in the failure analysis, in an emission image. For this image, the region setter 131 sets six analysis regions B1-B6 corresponding to the emission regions, as shown in (b) in FIG. 3.

In the present embodiment, this region setter 131 has an analysis region setter 136 and a mask region setter 137. The analysis region setter 136 is a setting means for setting an analysis region by applying a predetermined intensity threshold to the failure observed image P2. For example, in a schematic example shown in (a) in FIG. 4, there are three emission parts in an emission image being the failure observed image P2.

With this failure observed image P2, the analysis region setter 136 compares an intensity distribution in the image P2 with the predetermined intensity threshold and selects, for example, pixels having respective intensity values not less than the intensity threshold. This results in extracting reaction regions A1-A3 as reaction information contained in the failure observed image P2, as shown in (b) in FIG. 4. When the failure observed image P2 herein is an emission image, the intensity distribution in the image P2 corresponds to an emission intensity distribution in the semiconductor device. The reaction regions A1-A3 extracted based on the intensity threshold correspond to the emission regions.

Furthermore, the analysis region setter 136 sets analysis regions B1-B3 used in the failure analysis of the semiconductor device, corresponding to the reaction regions A1-A3 extracted as described above. Such setting of analysis regions is preferably carried out by hand in accordance with operator's input through the input device 45 using a keyboard, a mouse, and so on. Alternatively, the analysis region setter 136 may be arranged to perform the setting automatically. There are no particular restrictions on the shape of the set analysis regions, but the shape to be set is preferably a rectangular region (reaction box) as shown in (b) in FIG. 3 and in (b) in FIG. 4, in terms of easiness of analysis or the like.

Specific setting methods of analysis regions may be various methods, in addition to the above-described method of applying the intensity threshold. For example, instead of setting the analysis regions after extraction of the reaction regions from the failure observed image, it is also possible to adopt a method of setting the analysis regions automatically or manually by an operator, directly from the failure observed image.

The mask region setter 137 is a setting means for setting a mask region used as a mask on the occasion of performing the failure analysis using the failure observed image. Using the failure observed image masked by the mask region set by the mask region setter 137, the analysis region setter 136 performs the extraction of the reaction regions and the setting of the analysis regions with reference to the masked failure observed image. The setting of the mask region and the masking process on the failure observed image are not essential and may be omitted if unnecessary.

The interconnection information analyzer 132 is an analyzing means for performing an analysis on a plurality of nets (a plurality of interconnections) included in the layout of the semiconductor device, with reference to the analysis regions set by the analysis region setter 136. Specifically, the interconnection information analyzer 132 performs a necessary analysis on the plurality of interconnections and extracts an interconnection passing the aforementioned analysis regions, as a candidate interconnection (candidate net) for a failure (interconnection information analyzing step). Furthermore, where the analysis region setter 136 sets a plurality of analysis regions, the interconnection information analyzer 132 may extract each candidate interconnection passing at least one of the plurality of analysis regions, out of the plurality of interconnections, and also extract a passage count of the extracted candidate interconnection through the analysis regions (the number of analysis regions where the interconnection passes).

In the example described above, as shown in (c) in FIG. 3, four interconnections C1-C4 are extracted as candidate interconnections passing the analysis regions, with the six analysis regions B1-B6 set by the analysis region setter 136. Among these candidate interconnections C1-C4, the interconnection C1 has the largest passage count of 3 through the analysis regions, the interconnection C2 the passage count of 2, and each of the interconnections C3, C4 the passage count of 1.

In this analysis of interconnection information, it is preferable to execute the analysis, while carrying out communication with the layout information supplying apparatus 30 through the layout information acquirer 12 as occasion may demand. An example of this configuration is such that the interconnection information analyzer 132 is arranged to instruct the layout information supplying apparatus 30 to extract candidate interconnections and to acquire the passage counts through the analysis regions, and to receive the result thereof.

In the present embodiment, specifically, the interconnection information analyzer 132 executes the interconnection analysis by making use of the interconnection information about a plurality of interconnections, which is retained in the layout information supplying apparatus 30 or which is supplied from the layout information supplying apparatus 30 to the failure analysis apparatus 10, as the information about the layout of the semiconductor device. The present embodiment utilizes as this interconnection information, the interconnection information acquired from the aforementioned GDSII data or the like as to the layout information supplying apparatus 30. In such interconnection information, a configuration of a plurality of interconnections in a semiconductor device is described by a pattern data group of interconnection patterns represented by figures in the respective layers in the layer structure of the semiconductor device.

The interconnection information analyzer 132 utilizes this interconnection information in the extraction of the candidate interconnection for the failure carried out with reference to the analysis region, and performs the equipotential trace of the interconnection patterns using the pattern data group to extract the candidate interconnection. Namely, in the aforementioned interconnection information, the structure of interconnections in the semiconductor device is described as an aggregate of interconnection patterns. Therefore, when the equipotential trace is executed through a plurality of layers for such interconnection patterns, every interconnection as an analysis object can be extracted.

The interconnection information analyzer 132 may also be arranged to perform a process of selecting a failure interconnection (suspect failure interconnection) with a high possibility of a failure in fact, out of the plurality of candidate interconnections extracted as described above, according to need. A specific selection method of such a failure interconnection (failure net) is, for example, as follows; a candidate interconnection with the largest passage count through the analysis regions is selected as a likeliest suspect interconnection out of the plurality of extracted candidate interconnections to be defined as a first failure interconnection. Furthermore, in selection of the next suspect failure interconnection, a second failure interconnection is selected with attention to the analysis regions where the first failure interconnection does not pass. The interconnection information analyzer 132 further selects a third failure interconnection and subsequent interconnection by a similar method if necessary.

In the present embodiment, an analysis object selector 135 is further provided relative to the interconnection information analyzer 132. The analysis object selector 135 is a selecting means for selecting a layer as an object for the failure analysis in the interconnection information analyzer 132, according to need, for a layer structure of the semiconductor device as an object for the failure analysis. This selection of the layer by the analysis object selector 135 can be performed, for example, with reference to an acquisition condition of the failure observed image or the like.

The analysis screen display controller 14 lets the display device 40 display the information such as the images necessary for the failure analysis, or the information obtained as the analysis result, as an analysis screen according to need. Particularly, in the present embodiment, the analysis screen display controller 14 lets the display device 40 display information indicating the analysis result by the failure analyzer 13 as described above, e.g., information about the reaction regions extracted by the analysis region setter 136 and the analysis regions set corresponding to the reaction regions, or information about the interconnections extracted by the interconnection information analyzer 132 and the passage counts of the respective interconnections through the analysis regions (information display controlling step).

The display of the analysis result may be implemented, for example, by displaying an image containing the analysis regions and interconnections as shown in (c) in FIG. 3, or by displaying names of the interconnections and counts of passages or the like. Specifically, the analysis screen display controller 14 preferably lets the display device 40 display an interconnection list to display a list of interconnections extracted by the interconnection information analyzer 132, as the analysis result.

Where a plurality of analysis regions are set, it preferably lets the display device 40 display an interconnection list to display a list of candidate interconnections (e.g., names of interconnections set arbitrarily) extracted by the interconnection information analyzer 132, and the passage counts of the interconnections through the analysis regions (e.g., counts indicating passages), as the analysis result. This permits the operator performing the failure analysis of the semiconductor device, to perform the analysis work by the interconnection information analyzer 132, with good visibility. The passage counts of the interconnections through the analysis regions may be displayed as a graph of passage counts, with further improvement in the visibility thereof.

Figure 5:
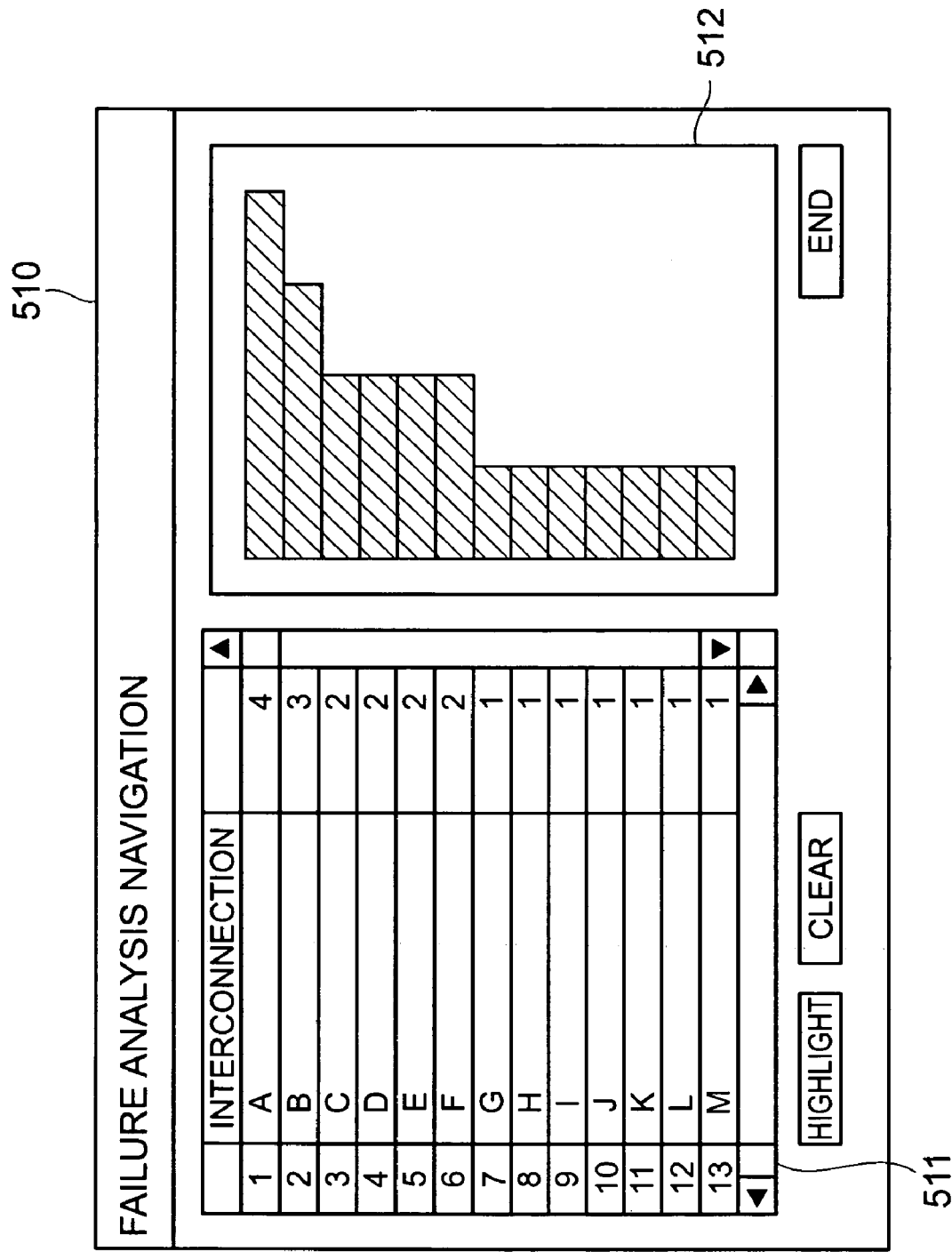
FIG. 5 is a configuration diagram showing an example of a display window.

The interconnection list can be displayed using an interconnection list display window shown in FIG. 5, for example. The display window 510 shown in FIG. 5 has an interconnection list display region 511 located on the left side of the screen, and a graph display region 512 displaying a graph (histogram) of the list of interconnections, which is located on the right side of the screen. The use of this display window 510 facilitates operator's understanding of the analysis result.

Where the analysis result is displayed by an image including the set analysis regions and the extracted interconnections, the extracted interconnections (nets) may be indicated by highlight display on the layout image, as shown in (c) in FIG. 3. It is also possible to use a variety of specific display methods; e.g., where one of the extracted nets is selected by manipulation of a mouse or the like, the analysis regions where the net passes are displayed by a different color. The reaction regions and the analysis regions may be displayed as follows; for example, as shown in (b) in FIG. 4, they are displayed by an image indicating both the reaction regions and analysis regions, or they are displayed by an image indicating either the reaction regions or the analysis regions.

The failure analyzer 13 of the present embodiment is provided with a position adjuster 133, corresponding to the configuration wherein the inspection information acquirer 11 acquires the pattern image P1 in addition to the failure observed image P2. The position adjuster 133 performs position adjustment between the observed images from the inspection information supplying apparatus 20 including the pattern image P1 and the failure observed image P2, and the layout image P3 from the layout information supplying apparatus 30, with reference to the pattern image P1 and the layout image P3 (position adjustment step). This position adjustment can be performed, for example, by a method of designating three appropriate points in the pattern image P1, further designating three corresponding points in the layout image P3, and performing the position adjustment from coordinates of those points.

The failure analyzer 13 is provided with an additional analysis information acquirer 134. The additional analysis information acquirer 134 acquires additional analysis information about the failure of the semiconductor device acquired by another analysis method than the aforementioned analysis method by the region setter 131 and the interconnection information analyzer 132, from an external device or the like (additional analysis information acquiring step). This additional analysis information acquired is referenced in combination with the analysis result acquired by the interconnection information analyzer 132.

The effects of the semiconductor failure analysis apparatus and semiconductor failure analysis method according to the above embodiment will be described below.

The semiconductor failure analysis apparatus 10 shown in FIG. 1, and the failure analysis method are arranged to acquire the failure observed image P2 obtained by inspecting the semiconductor device as an analysis object, and the necessary information about the layout of the semiconductor device, through the inspection information acquirer 11 and the layout information acquirer 12. Then the region setter 131 sets the analysis region in correspondence to the reaction information caused by a failure in the failure observed image P2 (e.g., information about a reaction part, specifically, information about an emission part in an emission image or the like), and the interconnection information analyzer 132 extracts a net passing the analysis region out of the interconnections constituting the semiconductor device, thereby performing the analysis of the failure of the semiconductor device.

This configuration permits the apparatus and method to estimate an interconnection with a high possibility of a failure (suspect failure interconnection) in the semiconductor device out of the huge number of interconnections in the semiconductor device, by suitably setting an analysis region (e.g., a rectangular reaction box) and extracting a net passing the analysis region. For example, the reaction information arising from the failure in the failure observed image P2 contains not only a case where the reaction part itself is a failure part, but also a part where reaction occurs due to another failure part, for example, a failure interconnection or the like. The above configuration permits the apparatus to suitably perform narrowing and estimation with the use of the analysis region, for such failure interconnections or the like as well.

Furthermore, the above configuration uses the interconnection information to describe the configuration of the plurality of interconnections by the pattern data group being an aggregate of interconnection patterns in the respective layers in the layer structure, as data indicating the interconnection configuration in the semiconductor device. In the extraction of the candidate interconnection for the failure, the equipotential trace of the interconnection patterns is then carried out in the pattern data group to extract the candidate interconnection. This configuration is able to efficiently execute the extraction of the candidate interconnection for the failure, using the interconnection information, for example, obtained from the GDSII data easier to acquire than the DEF/LEF data. Therefore, it becomes feasible to securely and efficiently perform the failure analysis of the semiconductor device using the failure observed image.

The failure analysis system 1 composed of the above-described semiconductor failure analysis apparatus 10, inspection information supplying apparatus 20, layout information supplying apparatus 30, and display device 40 substantializes a semiconductor failure analysis system capable of securely and efficiently carrying out the analysis of the failure of the semiconductor device with the use of the failure observed image P2.

A specific extraction method of a candidate interconnection by the equipotential trace executed in the interconnection information analyzer 132 of the failure analyzer 13 is preferably as follows; among a plurality of layers in a semiconductor device, a search layer used in extraction of the candidate interconnection passing the analysis regions, and a trace layer used in the equipotential trace of the interconnection patterns are set and the extraction of the candidate interconnection is then executed. When the search layer and the trace layer each are set according to the specific layer structure and device structure or according to a type of the failure observed image P2 used in the analysis or the like, among the plurality of layers constituting the semiconductor device as described above, it is feasible to suitably execute the extraction of the candidate interconnection by the equipotential trace of the interconnection patterns.

A specific extraction method of a candidate interconnection is preferably configured as follows; among a plurality of layers in a semiconductor device, a break layer where the equipotential trace of the interconnection patterns ends is set and the extraction of the candidate interconnection is then executed. When the break layer to terminate the equipotential trace is set among the plurality of layers forming the semiconductor device as described above, it becomes feasible to execute a variety of failure analyses, e.g., a method of designating a layer to which gates of transistors are connected, as a break layer, and separately detecting a light-emitting transistor.

In the configuration permitting the setting of the break layer as described above, the interconnection information analyzer 132 may be arranged to have a first mode of extracting only an interconnection terminated in the break layer, and a second mode of performing the extraction of the interconnection without reference to the break layer, as trace modes in the equipotential trace of the interconnection patterns. This configuration enables the apparatus and method to switch between the trace modes of the interconnection patterns, for example, according to an image acquisition condition of a failure observed image used in the failure analysis or according to a situation of occurrence of reaction in the semiconductor device. This improves the certainty of the failure analysis of the semiconductor device using the failure observed image P2.

Furthermore, the interconnection information analyzer 132 may also be arranged to be able to set a maximum number of extracted patterns to limit the number of extracted interconnection patterns (figures), as to the equipotential trace of the interconnection patterns. This makes it feasible to suitably execute the extraction of the candidate interconnection by the equipotential trace of the interconnection patterns using the interconnection information obtained from the GDSII data or the like. How to extract the candidate interconnection with the use of the pattern data group will be described later in further detail.

Concerning the setting of the analysis regions in the region setter 131 of the failure analyzer 13, the above embodiment is arranged to extract the reaction regions by applying the intensity threshold to the intensity distribution in the failure observed image being a two-dimensional image consisting of a plurality of pixels, and to set the analysis regions on the basis of the reaction regions. This makes it feasible to suitably set the analysis regions used in the failure analysis.

How to set each analysis region corresponding to a reaction region can be, for example, a method of setting the analysis region in such a rectangular shape as to circumscribe the reaction region extracted in the failure observed image. Another applicable method is a method of setting the analysis region in a state in which a blank space of a width w is added to each of the left, right, upper, and lower sides of the reaction region. Such addition of blank space is effective, for example, to a case where the analysis region needs to be set fairly wider than the reaction region in the failure observed image P2, with consideration to positional accuracy or the like of the stage on which the semiconductor device is mounted during acquisition of the observed image. The setting method of the analysis region may be any one of various methods other than these methods.

Where the reaction regions are extracted by applying the intensity threshold in the analysis region setter 136 as in the aforementioned example, it is also possible to adopt a method of selecting the reaction regions used in the setting of the analysis regions, by further comparing the areas of the reaction regions with a predetermined area threshold, and setting the analysis regions corresponding to the selected reaction regions. This makes it feasible to perform the setting of the analysis regions after regions unnecessary for the failure analysis (e.g., small regions due to noise or dust) are eliminated out of the extracted reaction regions. This improves the certainty of the failure analysis of the semiconductor device using the failure observed image.

Concerning the setting of the analysis regions in the analysis region setter 136, the analysis regions are preferably set in the layout coordinate system corresponding to the layout of the semiconductor device. When the analysis regions extracted from the failure observed image P2 are set in the layout coordinate system on the layout information side instead of the coordinate system on the image on the inspection information side, it becomes feasible to efficiently execute the extraction of the candidate interconnection by the equipotential trace from the plurality of interconnections included in the layout of the semiconductor device, with reference to the analysis regions set in the layout coordinate system.

When the analysis regions are expressed in the layout coordinate system, the scope of application can be expanded of the analysis regions in the failure analysis of the semiconductor device. This can increase degrees of freedom for specific analysis methods in the failure analysis of the semiconductor device using the analysis regions. Alternatively, the analysis regions may be set in the coordinate system on the image. The coordinate system on the image in the failure observed image P2 or the like is set, for example, corresponding to the stage coordinate system in the semiconductor inspection apparatus, as described above.

When the layout coordinate system is applied to the setting of the analysis regions as described above, the observed images of the semiconductor device, such as the pattern image P1 and the failure observed image P2, may also be stored after their coordinates are transformed into the layout coordinate system. The mutual relations among the pattern image P1, failure observed image P2, and layout image P3 are preferably based on positional adjustment between the observed images P1, P2 and the layout image P3.

FIG. 6 is a drawing schematically showing the correspondence among the observed images and the layout image of the semiconductor device, wherein (a) in FIG. 6 shows a correspondence relation among the pattern image P1, the failure observed image P2, and the layout image P3 and (b) in FIG. 6 shows a superimposed image P6 in which those pattern image P1, layout image P3, and failure observed image P2 are superimposed in this order. As shown in this FIG. 6, the pattern image P1 acquired as an observed image, and the layout image P3 of the semiconductor device have a certain correspondence relation. Therefore, the position adjuster 133 of the failure analyzer 13 is able to perform the position adjustment of images with reference to the correspondence relation of each part between the pattern image P1 and the layout image P3.

When the position adjustment with the layout image P3 is executed using the pattern image P1 acquired in a state in which it is adjusted in position with respect to the failure observed image P2, as described above, the accuracy of the failure analysis can be improved on the nets or the like included in the layout of the semiconductor device. A specific method of such position adjustment can be one of various methods, e.g., rotation of the pattern image P1 (θ correction), movement of the layout image P3 (fine adjustment of position), and zooming of the layout image (enlargement/reduction), according to need.

Concerning the failure analysis of the semiconductor device using the analysis region, the region setter 131 of the failure analyzer 13 is preferably arranged to be able to set an attribute for the analysis region. In this case, the interconnection information analyzer 132 may be arranged to determine whether the analysis region is to be used in extraction of interconnections (or to be used in the failure analysis), with reference to the attribute set for the analysis region.

Furthermore, where there are a plurality of analysis regions set, the region setter 131 is preferably arranged to be able to set attributes for the respective analysis regions. In this case, the interconnection information analyzer 132 may be arranged to determine whether each of the analysis regions is to be used in the extraction of interconnections and the acquisition of passage counts, with reference to the attributes set for the respective analysis regions.

The processing corresponding to the failure analysis method executed in the semiconductor failure analysis apparatus 10 shown in FIG. 1 can be implemented by a semiconductor failure analysis program for letting a computer execute the semiconductor failure analysis. For example, the failure analysis apparatus 10 can be constructed of a CPU for executing each of software programs necessary for the processing of semiconductor failure analysis, a ROM storing the software programs, and a RAM temporarily storing data during execution of the programs. The aforementioned failure analysis apparatus 10 can be substantialized by letting the CPU execute a predetermined failure analysis program in this configuration.

The program for letting the CPU execute each of processes for the semiconductor failure analysis can be recorded in a computer-readable recording medium and distributed in that form. Such recording media include, for example, magnetic media such as hard disks and flexible disks, optical media such as CD-ROM and DVD-ROM, magnetooptic media such as floptical disks, or hardware devices such as RAM, ROM, and semiconductor nonvolatile memories specially arranged to execute or store program commands.

Figure 7:
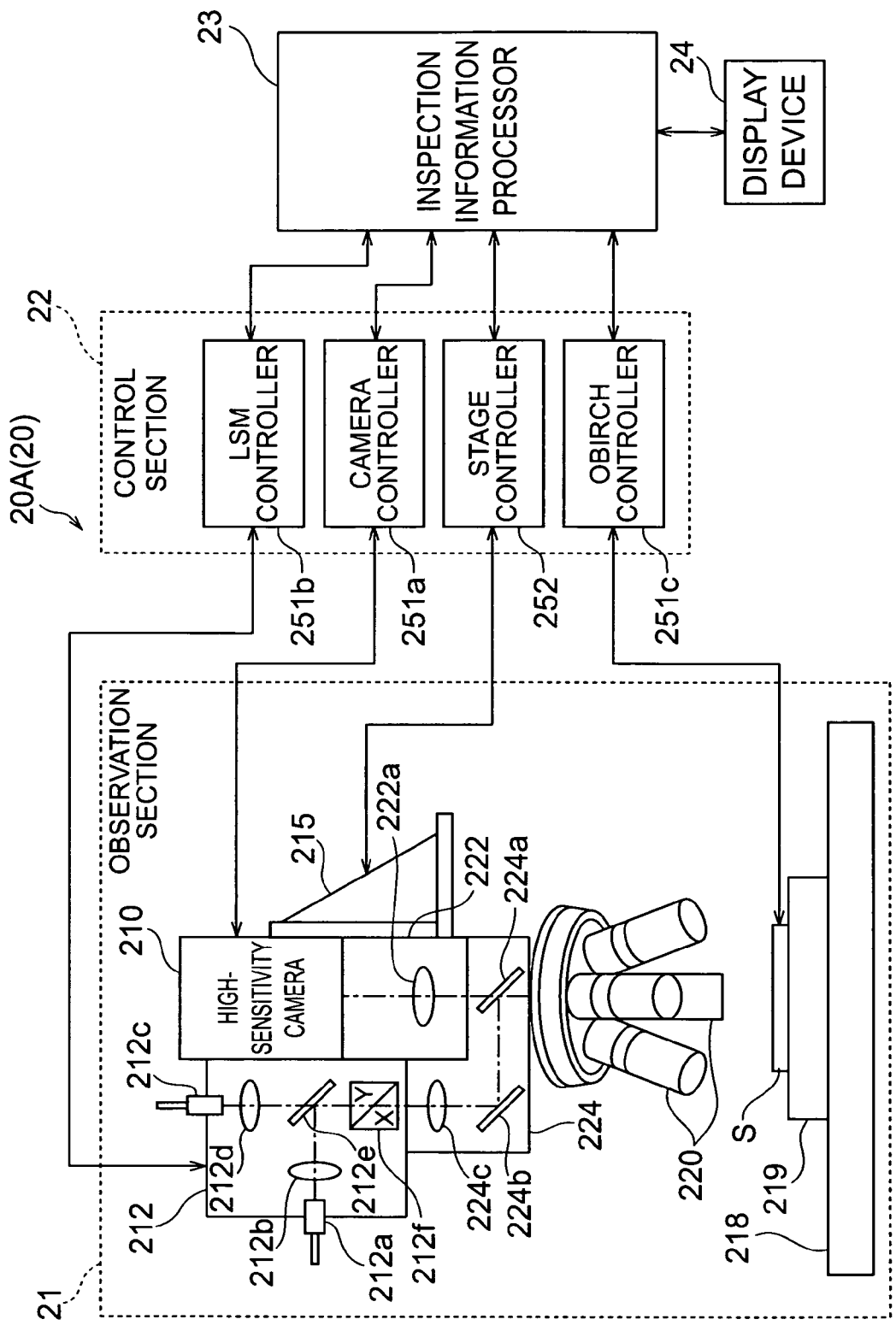
FIG. 7 is a configuration diagram showing an example of semiconductor inspection apparatus.
Figure 8:
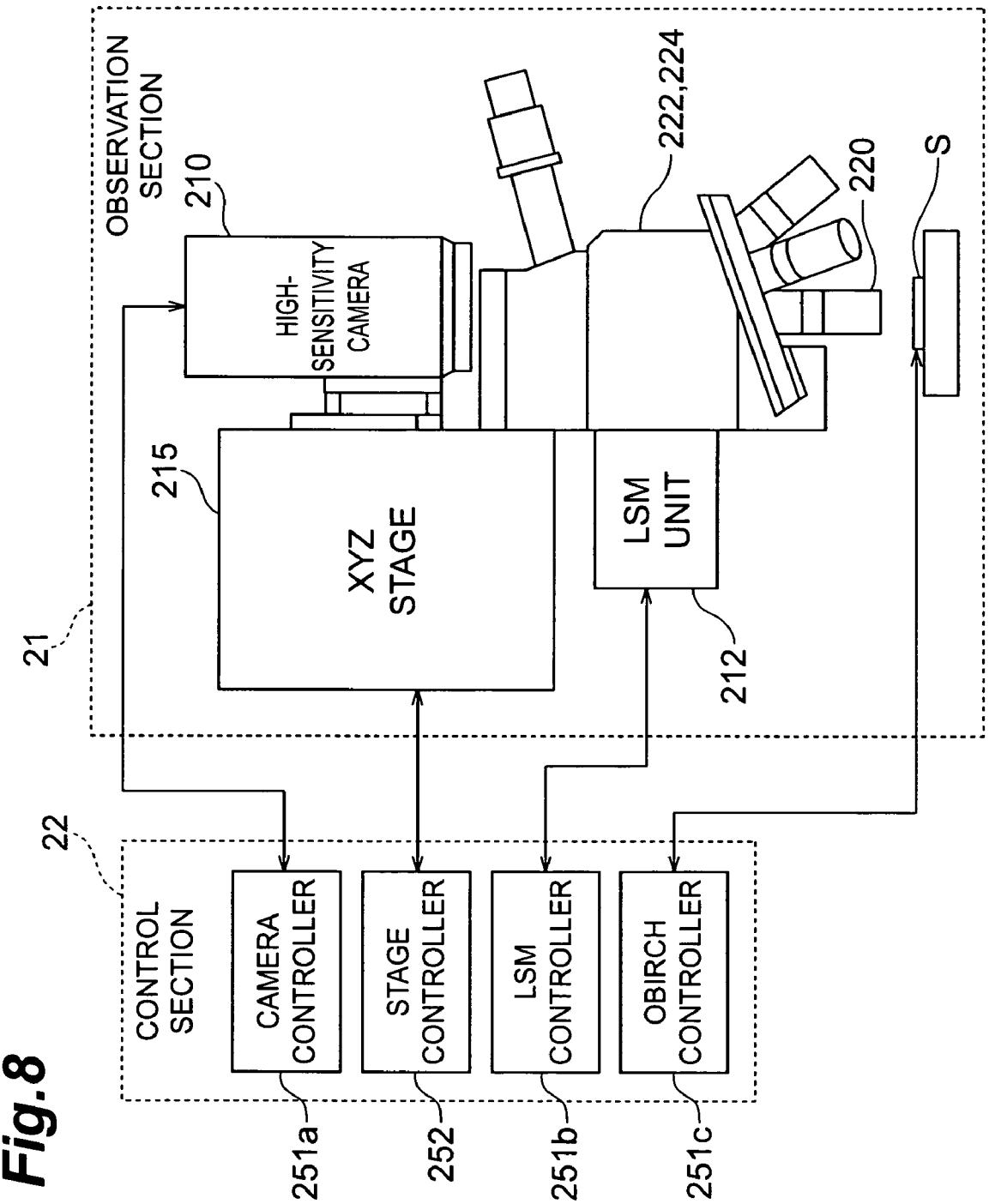
FIG. 8 is a configuration diagram as a side view of the semiconductor inspection apparatus shown in FIG. 7.

FIG. 7 is a configuration diagram showing an example of semiconductor inspection apparatus which can be applied as the inspection information supplying apparatus 20 shown in FIG. 1. FIG. 8 is a configuration diagram as a side view of the semiconductor inspection apparatus shown in FIG. 7.

The semiconductor inspection apparatus 20A according to the present configuration example comprises an observation section 21 and a control section 22. A semiconductor device S as an inspection object (analysis object to be analyzed by the failure analysis apparatus 10) is mounted on a stage 218 provided in the observation section 21. In the present configuration example, the apparatus is further provided with a test fixture 219 for applying an electric signal or the like necessary for the failure analysis to the semiconductor device S. The semiconductor device S is arranged, for example, so that a back face thereof faces an objective lens 220.

The observation section 21 has a high-sensitivity camera 210 set in a dark box, a laser scan optic (LSM: Laser Scanning Microscope) unit 212, optical systems 222, 224, and an XYZ stage 215. Among these, the camera 210 and LSM unit 212 are image acquiring means for acquiring an observed image of the semiconductor device S (pattern image P1 or failure observed image P2).

The optical systems 222, 224, and the objective lens 220 disposed on the semiconductor device S side of the optical systems 222, 224 constitute a lightguide optical system for guiding an image (optical image) from the semiconductor device S to the image acquiring means. In the present configuration example, as shown in FIGS. 7 and 8, a plurality of objective lenses 220 having their respective magnifications different from each other are arranged so as to be switchable from one to another. The test fixture 219 is an inspecting means for performing an inspection for the failure analysis of the semiconductor device S. The LSM unit 212 also has a function as an inspecting means, as well as the function as the aforementioned image acquiring means.

The optical system 222 is a camera optical system for guiding light from the semiconductor device S incident thereto through the objective lens 220, to the camera 210. The camera optical system 222 has an imaging lens 222a for forming an image enlarged at a predetermined magnification by the objective lens 220, on a light-receiving surface inside the camera 210. A beam splitter 224a of the optical system 224 is interposed between the objective lens 220 and the imaging lens 222a. The high-sensitivity camera 210 to be used is, for example, a cooled CCD camera or the like.

In this configuration, light from the semiconductor device S as a failure analysis object is guided through the optical system including the objective lens 220 and the camera optical system 222, to the camera 210. Then the camera 210 acquires an observed image such as the pattern image P1 of the semiconductor device S. It is also possible to acquire an emission image being a failure observed image P2 of the semiconductor device S. In this case, light generated from the semiconductor device S in a state in which a voltage is applied thereto by the test fixture 219 is guided through the optical system to the camera 210, and the camera 210 acquires an emission image.

The LSM unit 212 has a laser input optical fiber 212a for emitting an infrared laser beam, a collimator lens 212b for collimating the laser beam emitted from the optical fiber 212a, a beam splitter 212e for reflecting the laser beam collimated by the lens 212b, and an XY scanner 212f for emitting the laser beam reflected by the beam splitter 212e, to the semiconductor device S side, while scanning it in XY directions.

The LSM unit 212 further has a condenser lens 212d for condensing light incident thereto from the semiconductor device S side through the XY scanner 212f and transmitted by the beam splitter 212e, and a detection optical fiber 212c for detecting the light condensed by the condenser lens 212d.

The optical system 224 is an optical system for the LSM unit which guides light between the semiconductor device S and objective lens 220, and the XY scanner 212f of the LSM unit 212. The optical system 224 for the LSM unit has a beam splitter 224a for reflecting part of light incident thereto from the semiconductor device S through the objective lens 220, a mirror 224b for changing an optical path of the light reflected by the beam splitter 224a, into an optical path directed toward the LSM unit 212, and a lens 224c for condensing the light reflected by the mirror 224b.

In this configuration, the infrared laser beam emitted from a laser light source through the laser input optical fiber 212a passes the lens 212b, beam splitter 212e, XY scanner 212f, optical system 224, and objective lens 220 to irradiate the semiconductor device S.

Reflectively scattered light of this incident beam from the semiconductor device S reflects a circuit pattern provided in the semiconductor device S. The reflected light from the semiconductor device S passes through an optical path opposite to that of the incident beam to reach the beam splitter 212e, and passes through the beam splitter 212e. Then the light passing through the beam splitter 212e is incident through the lens 212d into the detection optical fiber 212c to be detected by a photodetector connected to the detection optical fiber 212c.

An intensity of the light detected through the detection optical fiber 212c by the photodetector is an intensity reflecting the circuit pattern provided in the semiconductor device S, as described above. Therefore, as the area on the semiconductor device S is scanned by X-Y scanning with the infrared laser beam by the XY scanner 212f, the pattern image P1 or the like of the semiconductor device S can be acquired as a clear image.

The control section 22 has a camera controller 251a, an LSM controller 251b, an OBIRCH controller 251c, and a stage controller 252. Among these, the camera controller 251a, LSM controller 251b, and OBIRCH controller 251c constitute an observation controlling means for controlling operations of the image acquiring means, inspection means, etc. in the observation section 21, thereby controlling the acquisition of the observed image of the semiconductor device S, the setting of observation conditions, etc. executed in the observation section 21.

Specifically, the camera controller 251a and LSM controller 251b control the operations of the high-sensitivity camera 210 and the LSM unit 212, respectively, to control the acquisition of the observed image of the semiconductor device S. The OBIRCH controller 251c is a controller for acquiring an OBIRCH (Optical Beam Induced Resistance Change) image which can be used as a failure observed image, and extracts an electric current change or the like in the semiconductor device S occurring during the scanning with the laser beam.

The stage controller 252 controls the operation of the XYZ stage 215 in the observation section 21, thereby controlling setting of an observed part in the semiconductor device S as an inspection part by the present inspection apparatus 20A, position adjustment thereof, focusing, and so on.

An inspection information processor 23 is provided for these observation section 21 and control section 22. The inspection information processor 23 performs such processing as data collection of the observed image of the semiconductor device S acquired in the observation section 21, supply of inspection information including the pattern image P1 and failure observed image P2, to the failure analysis apparatus 10 (cf FIG. 1), and so on. It is also possible to adopt a configuration wherein a display device 24 is connected to this inspection information processor 23 as occasion may demand. It is noted that FIG. 8 is illustrated without illustration of the inspection information processor 23 and the display device 24.

The semiconductor failure analysis apparatus, failure analysis method, and failure analysis program according to the present invention will be described in further detail.

Figure 9:
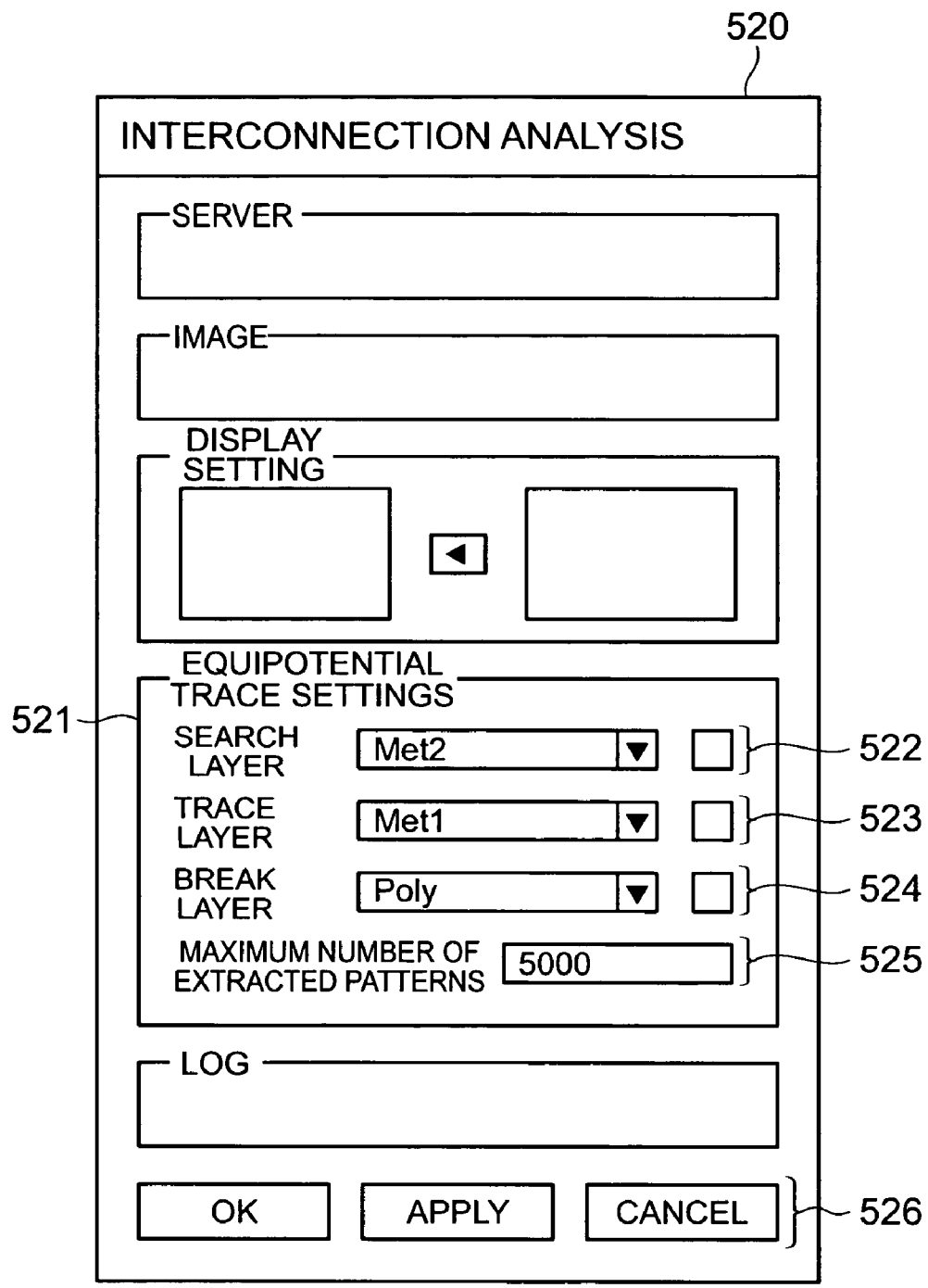
FIG. 9 is a configuration diagram showing an example of an extraction condition setting window.

First, a specific example will be described for the setting of extraction conditions for the candidate interconnection carried out in the interconnection information analyzer 132 of the failure analyzer 13 in the semiconductor failure analysis apparatus 10 shown in FIGS. 1 and 2. FIG. 9 is a configuration diagram showing an example of an extraction condition setting window used in the setting of the extraction conditions for the candidate interconnection, which is displayed on the display device 40.

In the example shown in FIG. 9, concerning the extraction process of the candidate interconnection by the equipotential trace executed in the interconnection information analyzer 132 of the failure analyzer 13, the operator is allowed to set as the extraction conditions for the candidate interconnection, a search layer used in extraction of the candidate interconnection passing the analysis regions, a trace layer used in the equipotential trace of the interconnection patterns, and a break layer to terminate the equipotential trace of the interconnection patterns, among the plurality of layers in the semiconductor device.

Specifically, the setting window 520 of FIG. 9 is provided with an equipotential trace setting region 521 consisting of three layer setting parts, search layer setting part 522, trace layer setting part 523, and break layer setting part 524. The interconnection information analyzer 132 performs the extraction of the candidate interconnection by the equipotential trace with reference to the search layer, trace layer, and break layer set in these setting parts 522-524.

The setting of the search layer is preferably to permit the operator to designate a plurality of layers in the layer structure of the semiconductor device. In a case where there is no need for designation of any layer in particular, all the layers may be set as search layers. Similarly, the setting of the trace layer is also preferably to permit the operator to designate a plurality of layers, and all the layers may be set as trace layers.

The break layer is set in a case where a termination process based on recognition of gate is implemented in the equipotential trace of the interconnections, and the apparatus is arranged to permit the operator to designate a break layer or a plurality of break layers if necessary. When a break layer is designated, the first mode of extracting only an interconnection terminated in the break layer is selected as a trace mode of the equipotential trace. In contrast to it, when there is no break layer designated, the second mode of extracting an interconnection without reference to the break layer is selected as a trace mode. In the example shown in FIG. 9, as described above, the break layer setting part 524 is arranged to also serve as a trace mode selecting part.

The equipotential trace setting region 521 is also provided with a maximum number of extracted patterns setting part 525, in addition to the aforementioned layer setting parts 522-524. When the maximum number of extracted patterns is set in this number of patterns setting part 525, the maximum number of interconnection figure patterns to be traced is limited in the execution of the equipotential trace of the interconnections. This setting part 525 is preferably arranged as follows; in a case where there is no need for limiting the maximum number of interconnection figure patterns, for example, "0" can be designated to set the maximum number of extracted patterns to infinity.

This setting window 520 is also provided with various setting regions for setting other necessary conditions in the execution of the interconnection analysis, in addition to the equipotential trace setting region 521. Below these setting regions, there is a button display region 526 indicating instruction buttons of an OK button, an apply button, and a cancel button.

Next, a specific example will be described for the extraction method of the candidate interconnection executed in the interconnection information analyzer 132 of the failure analyzer 13 in the semiconductor failure analysis apparatus 10 shown in FIGS. 1 and 2. FIGS. 10 to 17 are drawings showing an example of the extraction method of the candidate interconnection.

It is assumed herein that interconnection patterns constituting a pattern data group in the interconnection information are expressed by rectangular patterns on respective layers. As a specific example for description, the layer structure of the semiconductor device is considered to be a structure including the first metal layer (Met1), the second metal layer (Met2), the third metal layer (Met3), the fourth metal layer (Met4), and a polysilicon layer (Poly).

It is also assumed that the layer structure of the semiconductor device is provided with via 1 (Via1) for connection between Met1 and Met2, via 2 (Via2) for connection between Met2 and Met3, via 3 (Via3) for connection between Met3 and Met4, and a connection layer (Cont) for connection between Met1 and Poly, as layers for connection between the layers.

Figure 10:
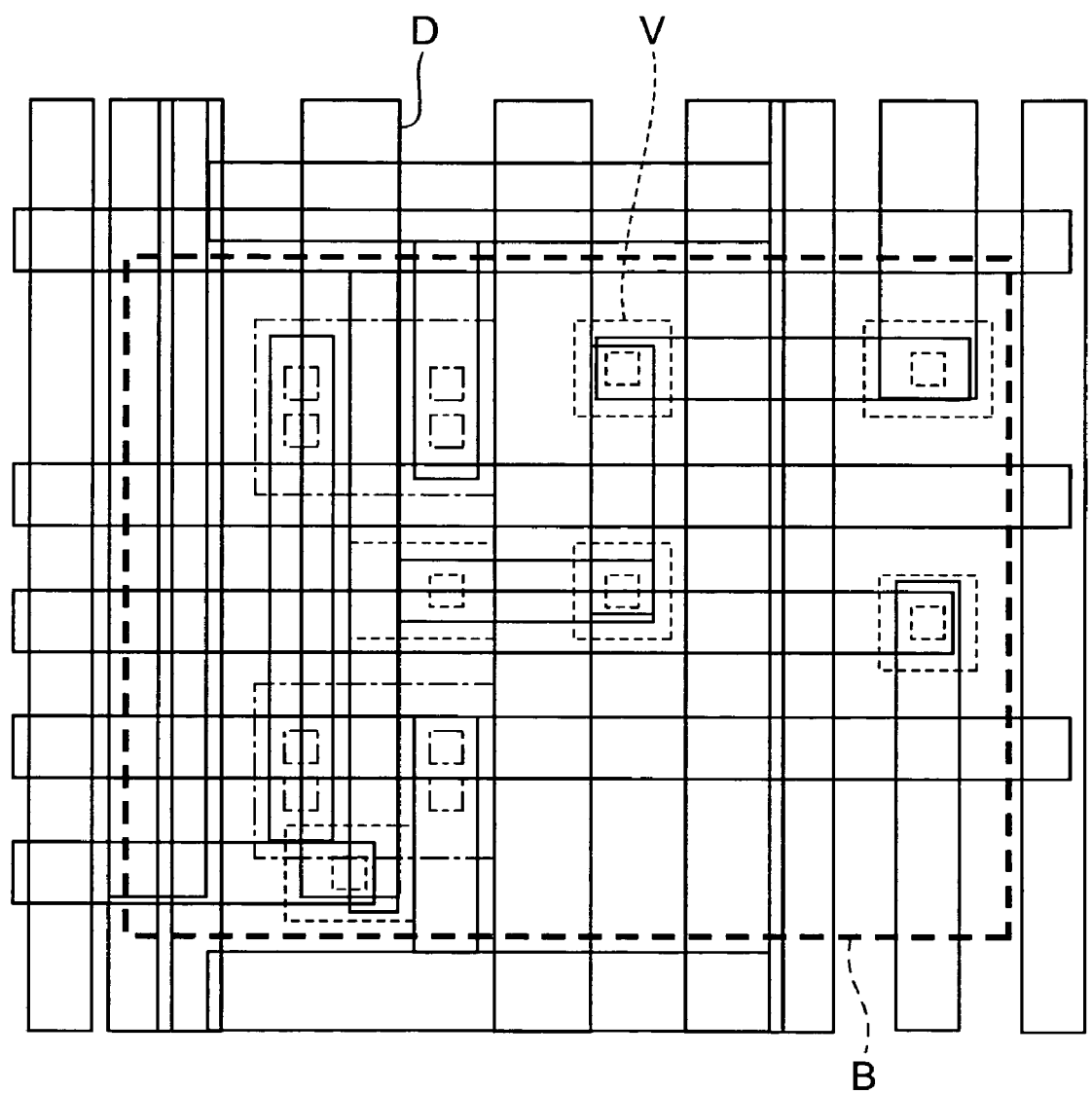
FIG. 10 is a drawing schematically showing an interconnection structure described by a pattern data group.

In this interconnection information, the configuration of the plurality of interconnections in the semiconductor device, as shown in FIG. 10, is described as a pattern data group being an aggregate of pattern data such as rectangular interconnection patterns D (solid lines) in the respective layers of the layer structure, and via patterns or contact patterns V (dashed lines) for connection between them. With the figure data of interconnections described in this manner, the equipotential trace of the interconnection patterns using the pattern data group is carried out across a plurality of layers, to extract necessary interconnections. An interconnection extracted by the equipotential trace is given an arbitrary name and, as to interconnections passing a plurality of analysis regions, preferably, the equipotential trace is not performed again for an interconnection extracted once, so as to achieve reduction of time.

Figure 11:
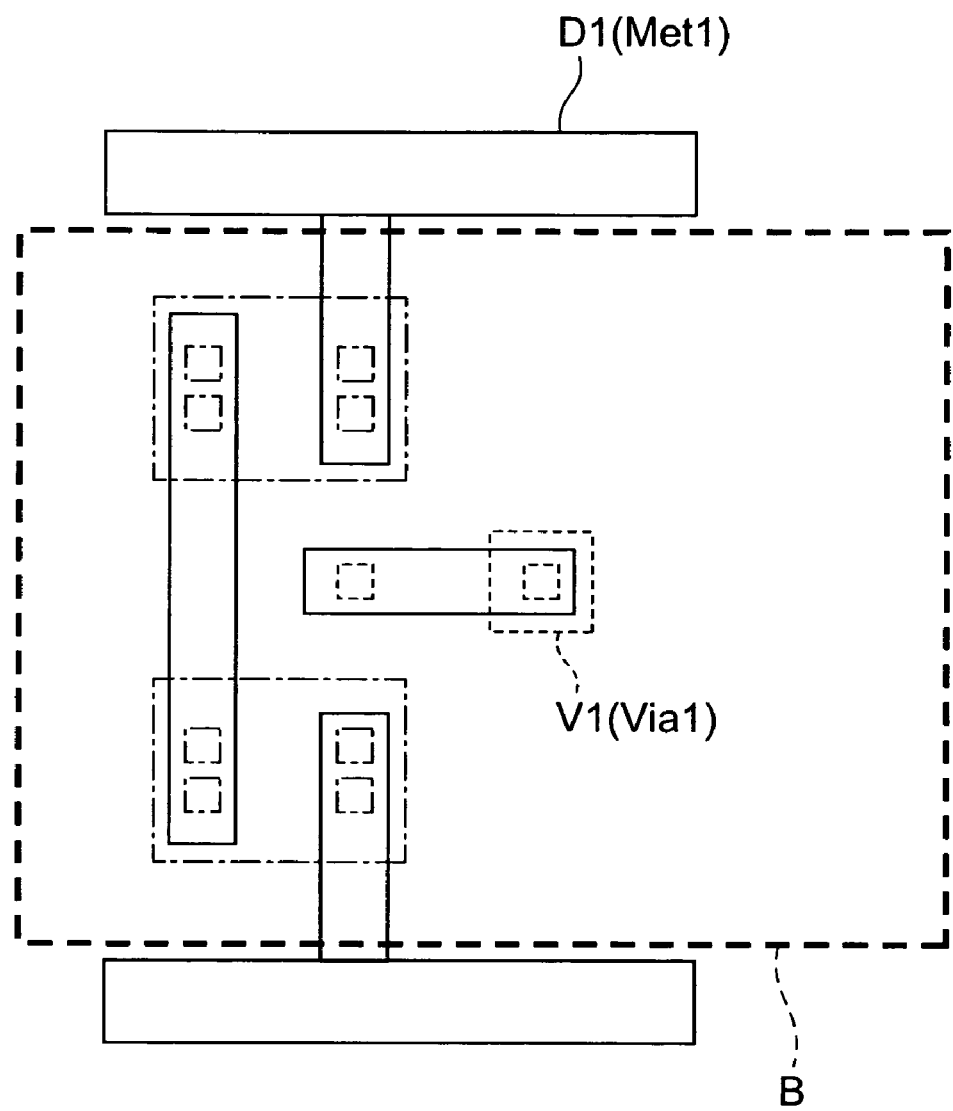
FIG. 11 is a drawing showing an interconnection pattern in a Met1 layer.
Figure 12:
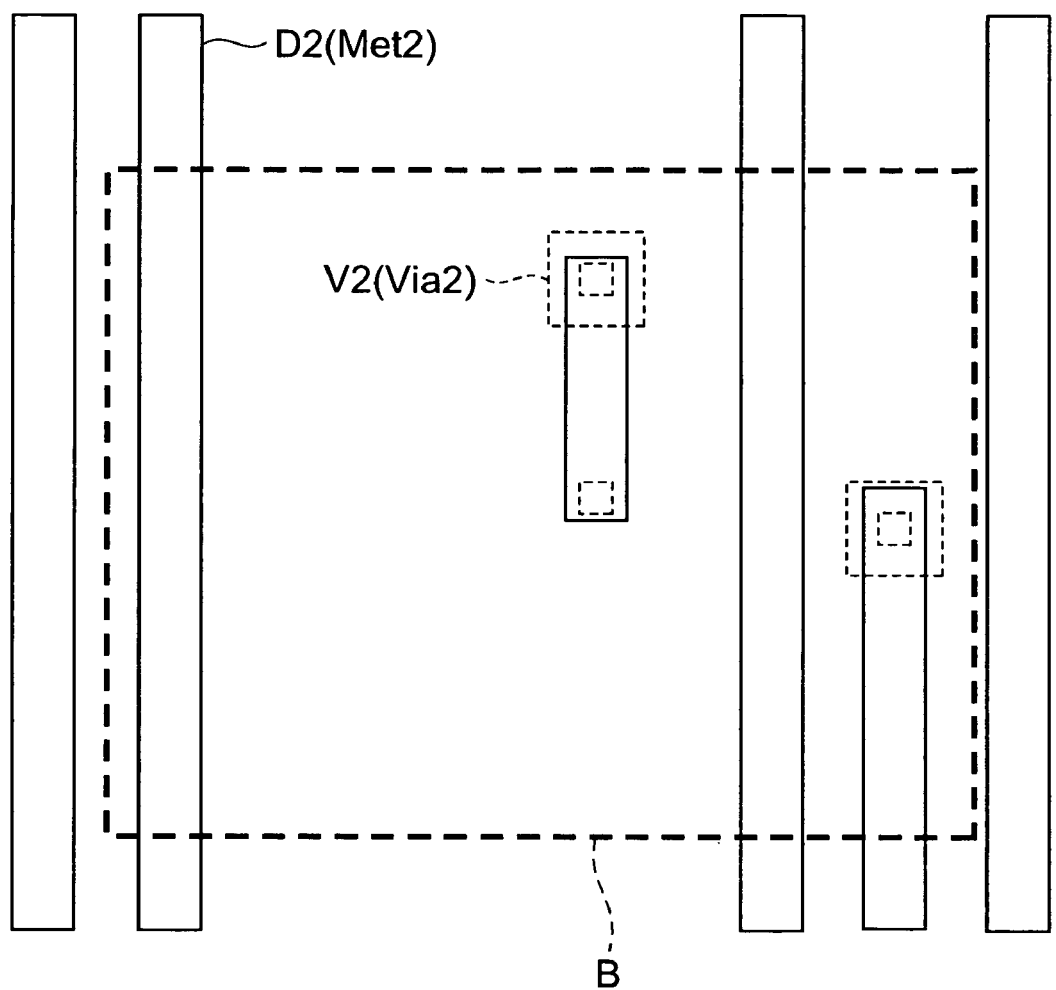
FIG. 12 is a drawing showing an interconnection pattern in a Met2 layer.
Figure 13:
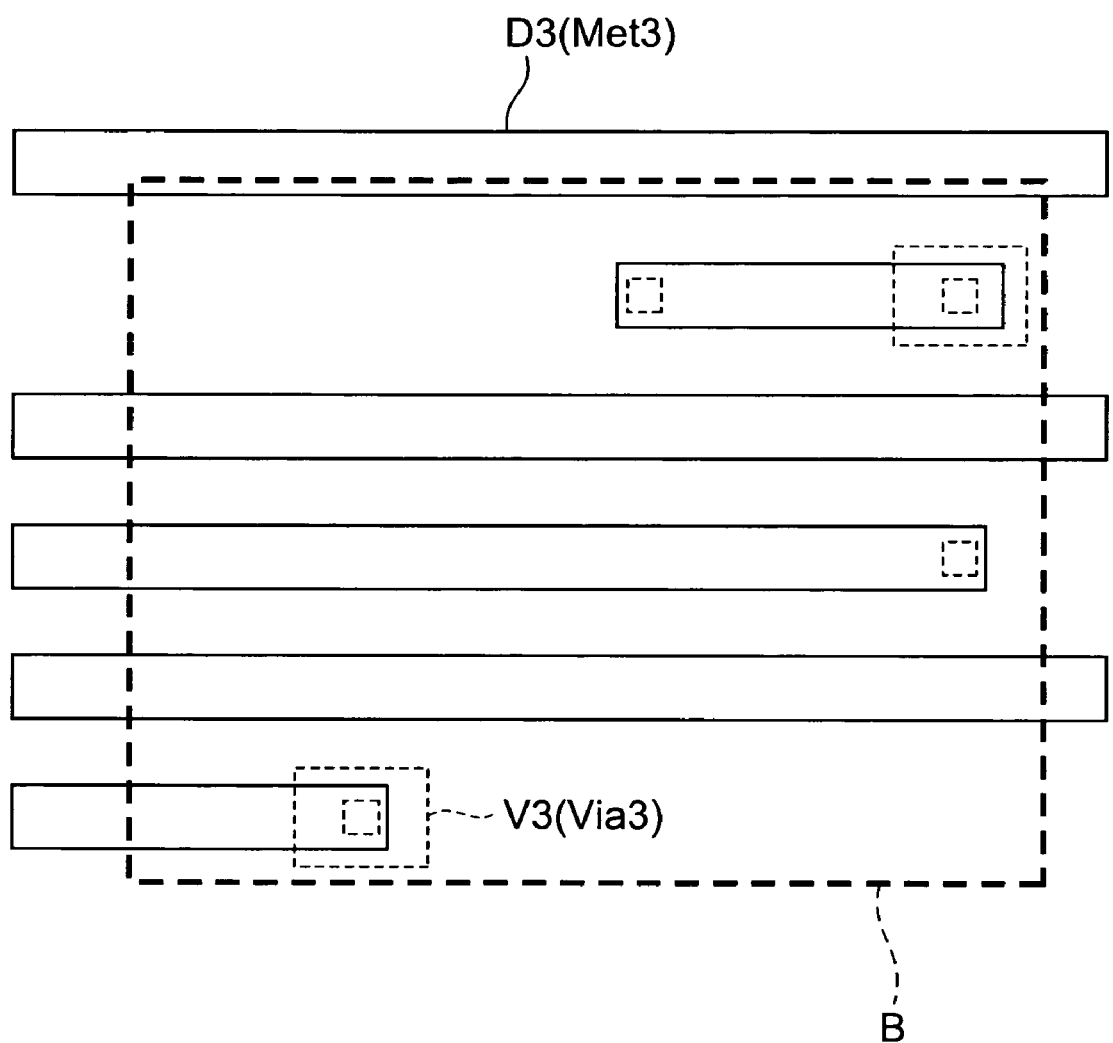
FIG. 13 is a drawing showing an interconnection pattern in a Met3 layer.
Figure 14:
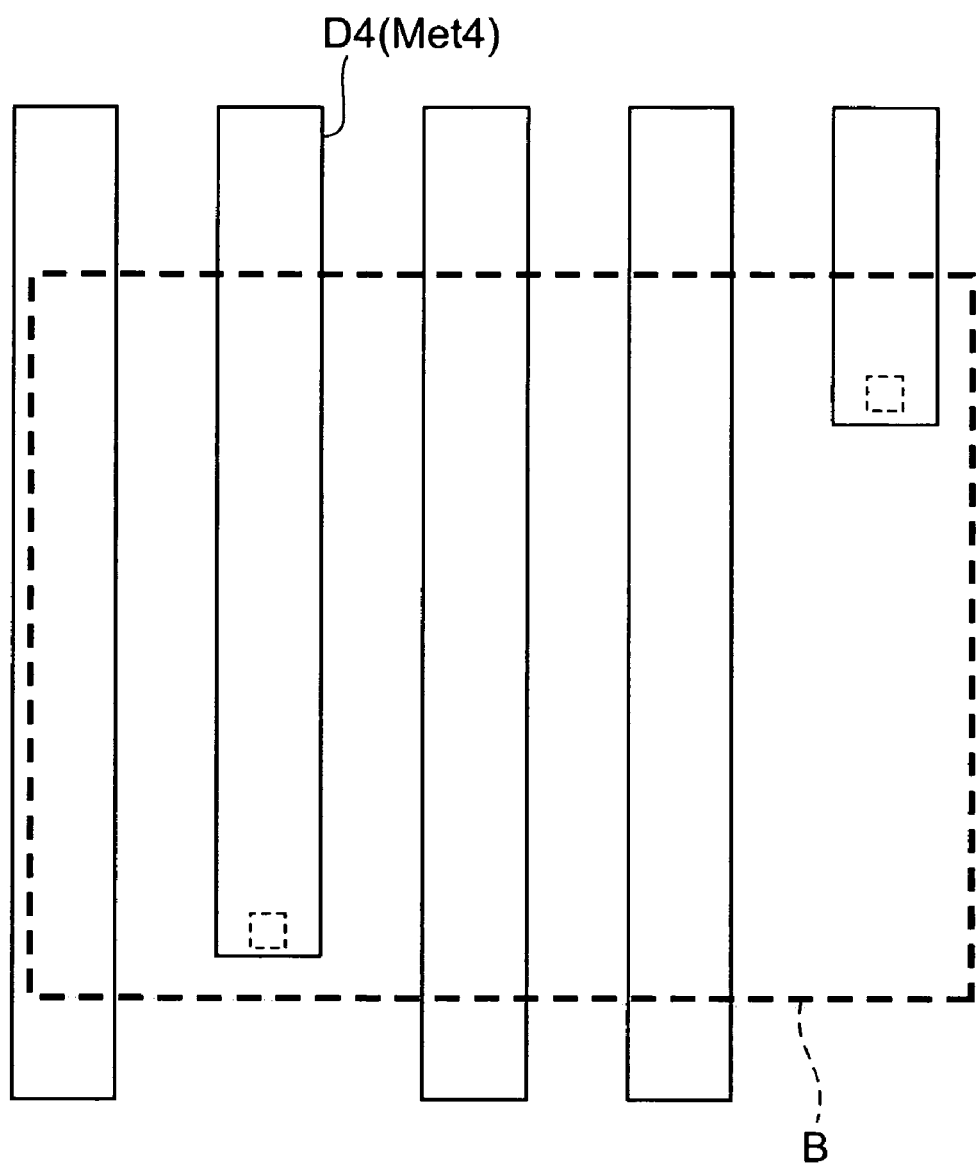
FIG. 14 is a drawing showing an interconnection pattern in a Met4 layer.
Figure 15:
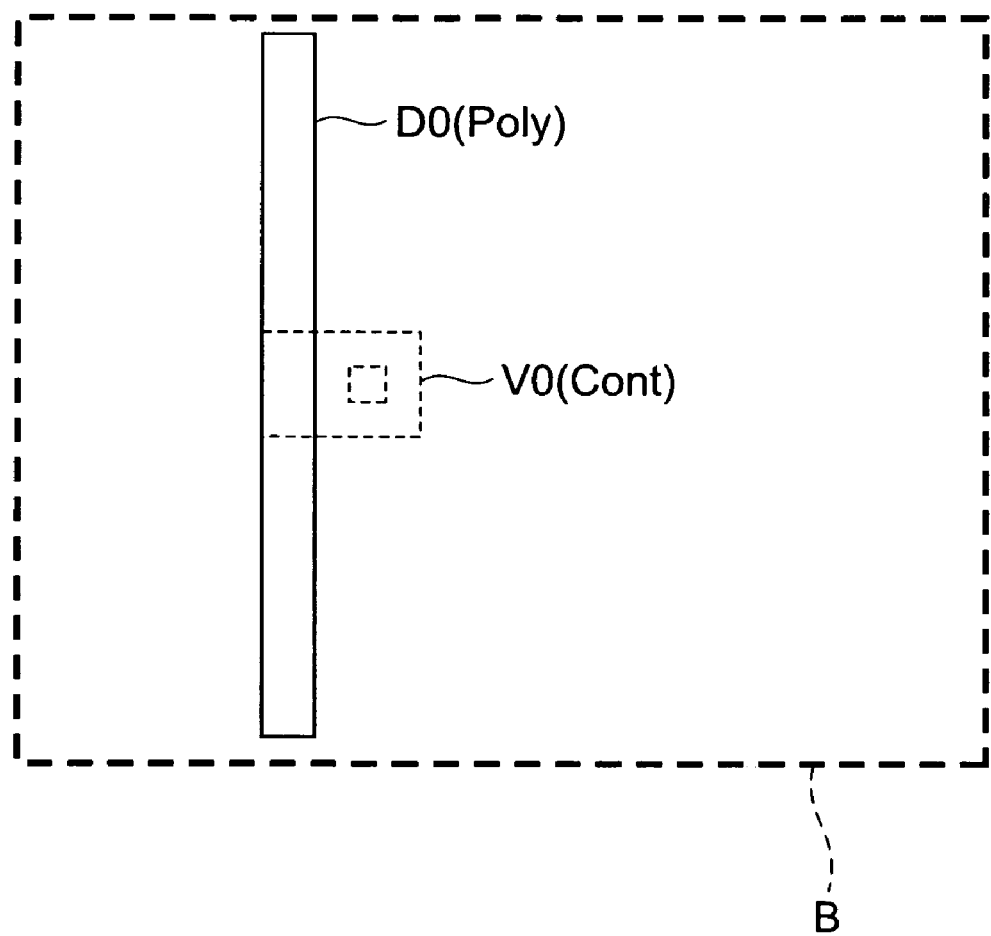
FIG. 15 is a drawing showing an interconnection pattern in a Poly layer.

FIGS. 11 to 15 are drawings showing decomposed views of structures in the respective layers from the interconnection structure shown in FIG. 10. FIG. 11 shows the interconnection pattern D1 in the Met1 layer, and the via pattern V1 in the Via1 layer for connection between Met1 and Met2. FIG. 12 shows the interconnection pattern D2 in the Met2 layer, and the via pattern V2 in the Via2 layer for connection between Met2 and Met3. FIG. 13 shows the interconnection pattern D3 in the Met3 layer, and the via pattern V3 in the Via3 layer for connection between Met3 and Met4. FIG. 14 shows the interconnection pattern D4 in the Met4 layer. FIG. 15 shows the interconnection pattern D0 in the Poly layer, and the contact pattern V0 in the Cont layer for connection between Met1 and Poly. In each of FIGS. 10 to 15, the rectangular region B indicated by a slightly thick dashed line indicates an analysis region set from the failure observed image and used in the extraction of the candidate interconnection.

Figure 16:
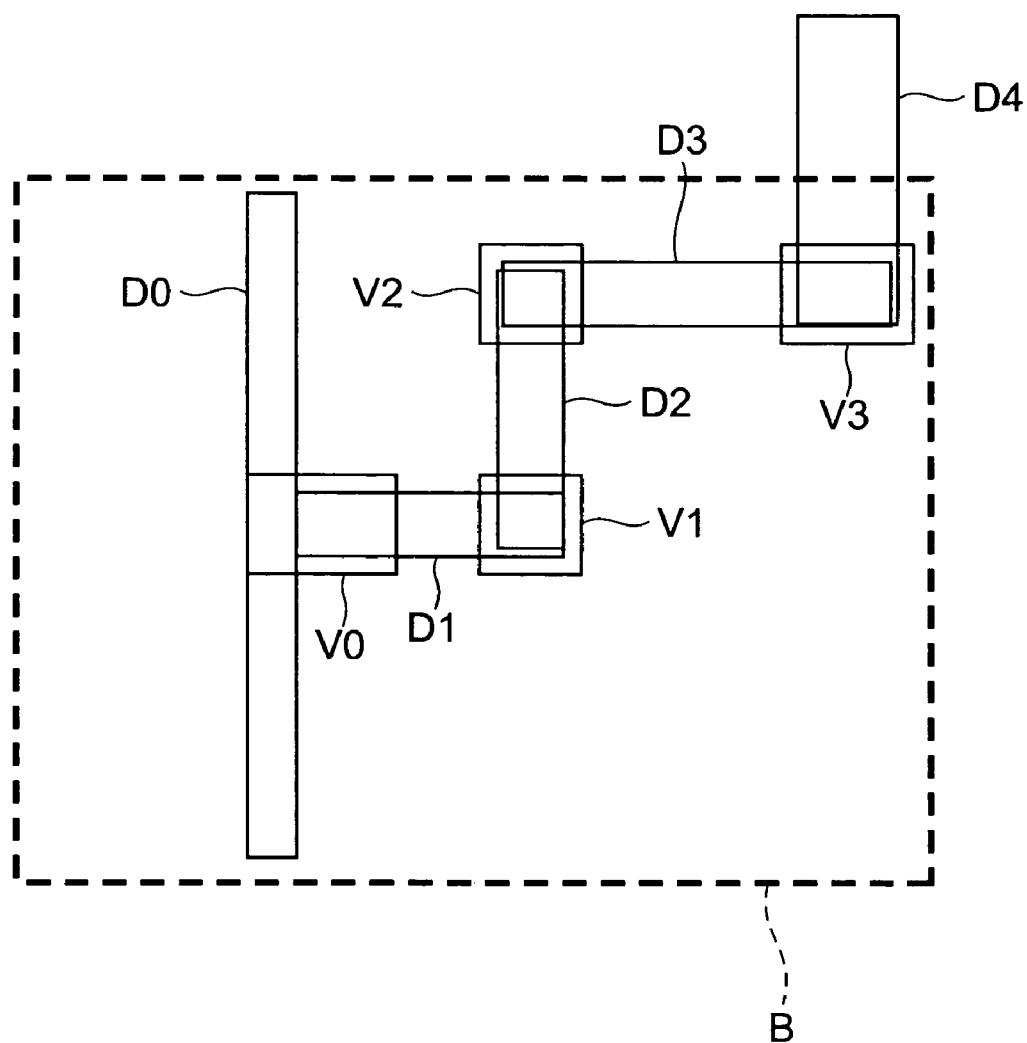
FIG. 16 is a drawing showing an example of an extraction result of a candidate interconnection by an equipotential trace.

With the pattern data group in the interconnection information as described above, the extraction of the candidate interconnection for the failure is carried out with reference to the analysis region B set in the failure observed image. FIG. 16 shows the result of the equipotential trace in such a setting that the two layers of Met2 and Met3 are set as search layers and that the five layers of Met1, Met2, Met3, Met4, and Poly are set as trace layers, as an example of the extraction result of the candidate interconnection by the equipotential trace.

This example shows the result of the equipotential trace in the trace mode with recognition of gate to extract only an interconnection terminated in the Poly layer, where Poly is set as a break layer. The polysilicon layer is a layer to which gates of transistors are connected. Therefore, when such a break layer is set, a light-emitting transistor can be separately detected. This configuration can improve the accuracy of the failure analysis of the semiconductor device.

Under such extraction conditions for the candidate interconnection, an interconnection pattern (passing the analysis region B) within the analysis region B is extracted as an interconnection pattern portion with a possibility of forming a candidate interconnection for a failure, out of the interconnection patterns D2, D3 in the Met2 layer and Met3 layer being the search layers. The equipotential trace is then carried out from a start point of the extracted interconnection pattern. This equipotential trace of the interconnection patterns is carried out for objects of interconnection patterns in the respective layers of Met1, Met2, Met3, Met4, and Poly being the trace layers, and with reference to the connection relations between them.

With the result of the equipotential trace, any interconnection not terminated in the Poly layer set as a break layer is excluded from candidate interconnections for a failure, and an interconnection terminated at the interconnection pattern D0 in the Poly layer is extracted as a candidate interconnection. In FIG. 16, an interconnection connected by interconnection patterns and vias in the respective layers in the order of D0-V0-D1-V1-D2-V2-D3-V3-D4 is extracted as a candidate interconnection.

Figure 17:
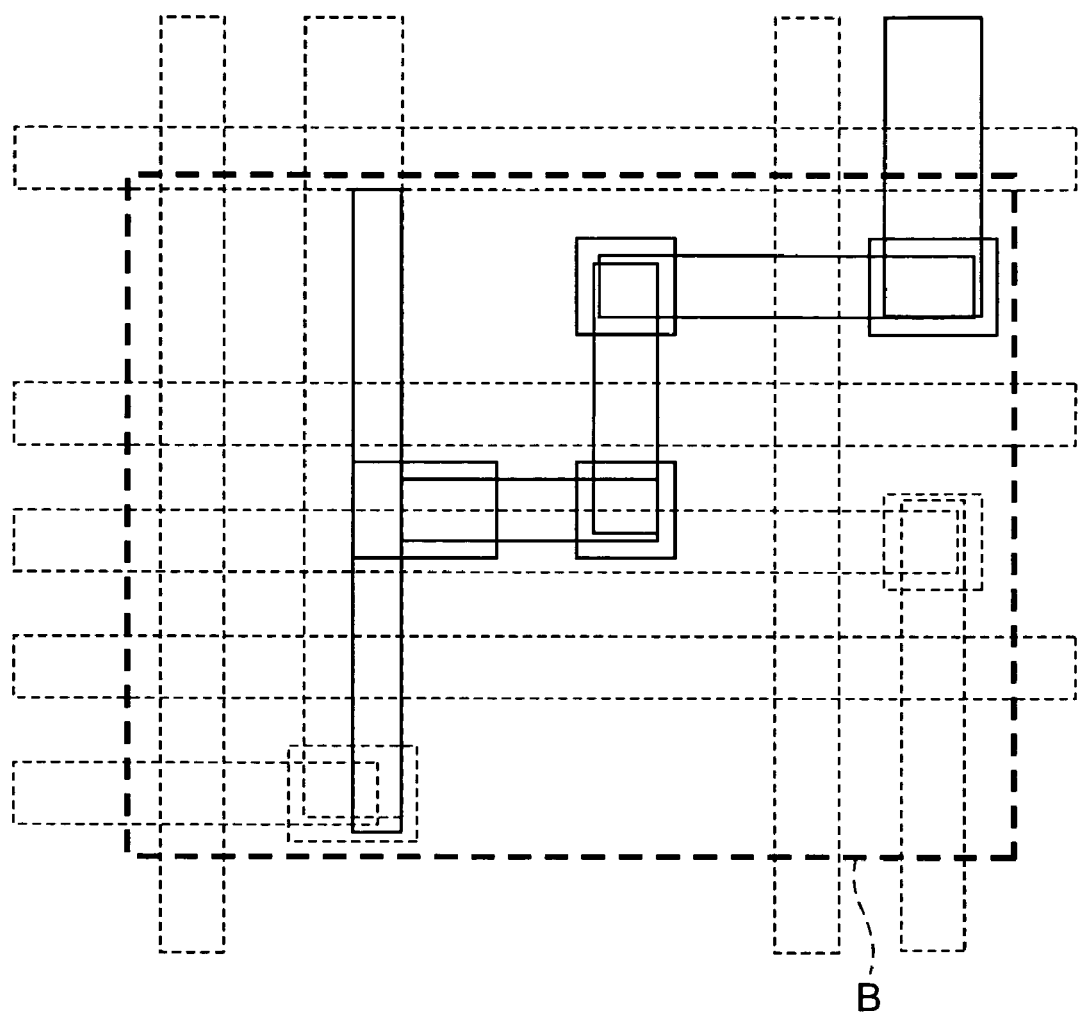
FIG. 17 is a drawing showing another example of an extraction result of a candidate interconnection by an equipotential trace.

FIG. 17 shows the result of the equipotential trace under such a setting that the two layers of Met2 and Met3 are set as search layers and that the five layers of Met1, Met2, Met3, Met4, and Poly are set as trace layers, as in the case of the above example of FIG. 16, as another example of the extraction result of the candidate interconnection by the equipotential trace. This example shows the result of the equipotential trace in the trace mode without recognition of gate for carrying out the extraction of the interconnection without reference to the break layer, where no break layer is set.

In FIG. 17, solid lines indicate an interconnection terminated in the Poly layer (interconnection shown in FIG. 16), and dashed lines the other extracted interconnections. In the mode without gate recognition, more interconnections are extracted as candidate interconnections than in the case with the gate recognition. The trace mode of the candidate interconnection is preferably selected on an as-needed basis according to a specific analysis condition, e.g., an acquisition condition for the failure observed image.

A specific trace method of candidate interconnection can be selected from a variety of methods, except for the above methods. For example, the above example described the method of focusing attention to gates of transistors in the equipotential trace of the interconnections using the GDSII data or the like, but, besides it, it is also possible to adopt a method of performing the interconnection analysis, for example, with attention to vias easy to cause resistance anomaly or open failure.

When the interconnection analysis is carried out with attention to transistors, it is also possible to provide an environment in which the operator of the failure analysis can readily estimate a failure part, by acquiring the number of terminal transistors at interconnections and displaying it in a list, or by displaying marks at locations of interconnection terminal transistors on the layout image as well. On the occasion of the equipotential trace for the candidate interconnection, it is also preferable to provide names of interconnections in design as names of extracted interconnections (equipotential lines). This permits an analysis in the transistor level along with the equipotential trace, and also enables a link with a failure diagnosis.

Next, the semiconductor failure analysis apparatus 10 shown in FIGS. 1 and 2 will be further described as to the region setting and others carried out by the region setter 131 of the failure analyzer 13.

In the above-described failure analysis apparatus 10, the analysis region setter 136 sets an analysis region and the failure analysis is carried out as to interconnections or the like in a semiconductor device with reference to this analysis region. When this analysis region is set as a region on the layout coordinate system as described above, the scope of application of the analysis region can be expanded; e.g., it becomes feasible to share the region data with the other data.

An example of such application of the analysis region is a method of defining as a standard an observed image acquired from a nondefective semiconductor device, and performing a masking process necessary for the failure observed image P2 in inspection of another semiconductor device, with reference to this standard observed image. In this case, for example, a specific method is such that the mask region setter 137 of the failure analyzer 13 sets a mask region with reference to the observed image of the nondefective semiconductor device. In connection therewith, the analysis region setter 136 is preferably arranged to perform the extraction of the reaction region and the setting of the analysis region, using the failure observed image P2 masked with the mask region set by the mask region setter 137.

When the mask region is set corresponding to a region arising from nondefective emission or the like, using the standard observed image acquired from an object such as a nondefective semiconductor device, it becomes feasible to set the analysis region after exception of the region not arising from a failure, out of the reaction regions extracted from the failure observed image. This improves the certainty of the failure analysis of the semiconductor device using the failure observed image.

For example, in a case where an analysis of open failure of the semiconductor device is carried out, the analysis of emission can be performed effectively in an operating state of LSI; in such analysis, emission often occurs in regions except for intrinsic failure parts. In addition thereto, emission can occur in regions except for the failure parts because of other causes. In such cases, the failure analysis for the intrinsic failure parts can be securely executed by performing the analysis of emission for the nondefective semiconductor device and performing the masking process for the failure observed image P2 with reference to the result of the analysis. A specific method of the masking process for the failure observed image P2 can be, for example, a method of setting the intensity of each pixel in the mask region to 0, or a method of erasing a reaction region and an analysis region in the mask region.

How to designate such a mask region may be selected from a variety of specific methods, e.g., a method of providing each region with a mask attribute. In a case where there are parts preliminarily expected to emit light, in terms of the layout in the semiconductor device, a mask region may be preliminarily set for such parts in the layout coordinate system. Concerning the masking process for the failure observed image, it is preferable to perform the masking process by carrying out processing of the image on a software basis as described above. In addition to such methods, the masking process may also be carried out on a hardware basis, for example, by a method of disposing a filter for masking (e.g., a liquid crystal mask a pattern of which can be controlled) between the semiconductor device and an image pickup device during acquisition of the observed image.

When the failure analysis is performed using the standard observed image acquired from the standard semiconductor device such as a nondefective device, together with the failure observed image, it is also effective to adopt a method of performing the failure analysis process by calculating a difference between the standard observed image and the failure observed image. Specifically, for example, the difference is calculated between analysis regions in a standard observed image of a nondefective device and analysis regions in a failure observed image of a defective device, and analysis regions including a common overlay portion are excluded out of the analysis regions set in the respective images. This permits us to extract inconsistent portions, e.g., the analysis regions with OFF in the nondefective device and ON in the defective device, and the analysis regions with ON in the nondefective device and OFF in the defective device, as suspect regions.

FIGS. 3 and 4 illustrate the emission image as the failure observed image P2 used in the failure analysis, but the similar failure analysis method can also be applied, for example, to cases where the failure observed image P2 is another observed image such as an OBIRCH image. The failure observed image can be an image obtained by a single observation under a single condition, but is not limited to it; for example, as shown in FIG. 18, the failure observed image may be one generated by superimposing a plurality of failure observed images acquired under respective different conditions.

In the example shown in FIG. 18, FIG. 18(a) shows a reaction region A1 extracted from an emission image acquired under a first condition, and an analysis region B1. FIG. 18(b) shows a reaction region A2 extracted from another emission image acquired under a second condition different from the first condition, and an analysis region B2. FIG. 18(c) shows a reaction region A3 extracted from an OBIRCH image, and an analysis region B3.

With these three types of failure observed images shown in (a) to (c) in FIG. 18, these images (analysis regions) are superimposed as shown in (d) in FIG. 18. This enables us to execute the failure analysis for net C by making use of the three analysis regions, the analysis regions B1-B3, as shown in (e) in FIG. 18. In such superposition of the failure observed images (superposition of analysis regions), it is also preferable to use the layout coordinate system as a common coordinate system to them.

In the failure analysis using the analysis regions, it is preferable to designate a layer as an analysis object in a semiconductor device, according to an occurrence situation of reaction in the semiconductor device, an image acquisition condition, and so on. This configuration permits us to select and designate a layer as an object for the failure analysis according to need, with reference to a specific acquisition method of the failure observed image or the like. This improves the certainty of the failure analysis of the semiconductor device using the failure observed image.

This method can be specifically, for example, as follows; in execution of the interconnection extraction with an analysis region being set, a desired layer is designated for extraction of an interconnection passing in the analysis region, and all the layers are designated for the failure analysis. This selection and designation of the layer can be implemented by use of the configuration in which the search layer and trace layer are set in the equipotential trace executed by the interconnection information analyzer 132, as described above. Alternatively, as shown in FIG. 2, the analysis object selector 135 for selecting a layer as an object for the failure analysis in the layer structure of the semiconductor device may be provided separately from the interconnection information analyzer 132 in the failure analyzer 13.

Figure 19:
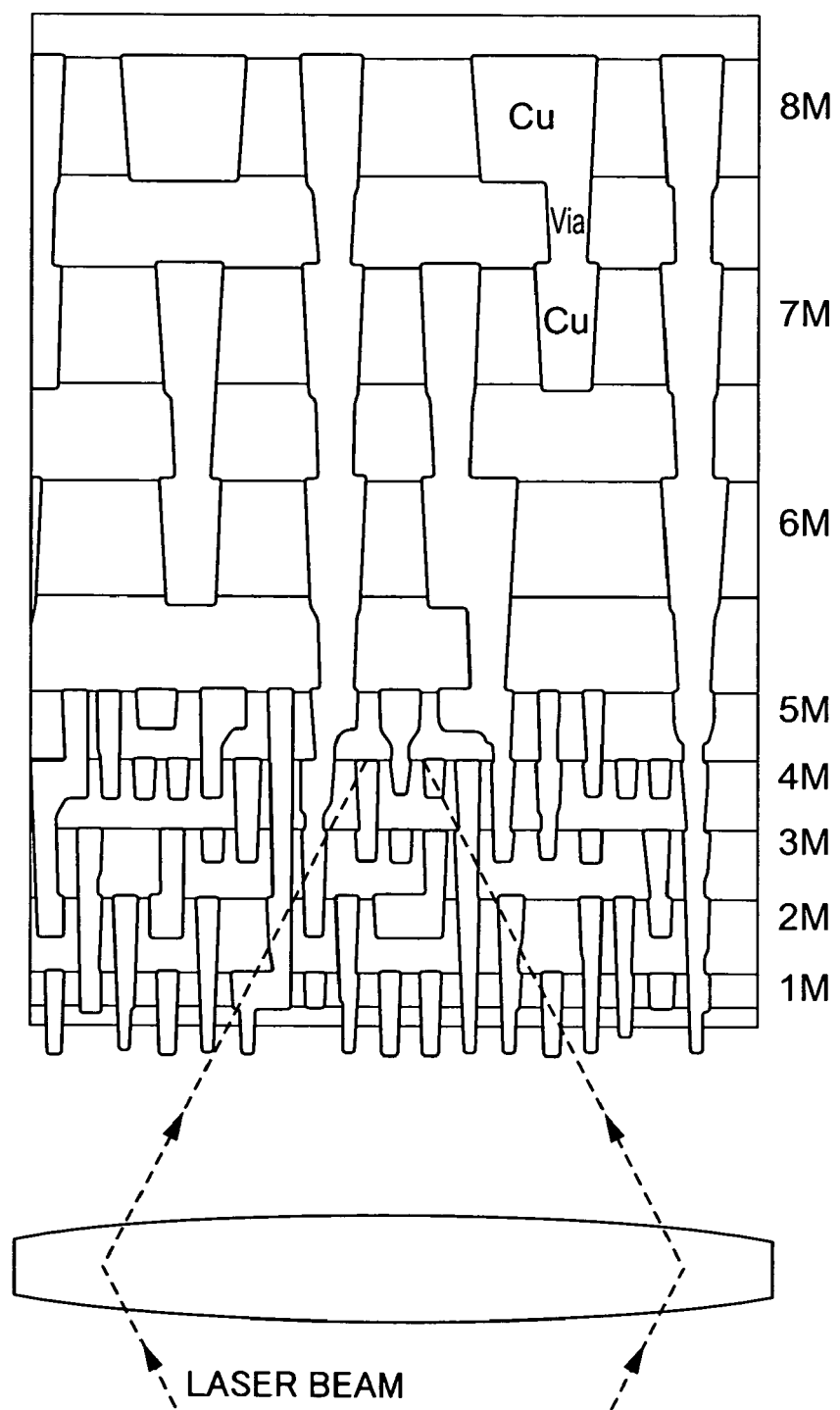
FIG. 19 is a drawing showing selection of a layer as an analysis object in an OBIRCH image.

FIG. 19 is a drawing showing an example of selection of a layer as an analysis object. Where an OBIRCH image is used as a failure observed image, as shown in FIG. 19, a reach of laser beam for measurement is limited in the layer structure of the semiconductor device. For example, when the analysis is performed from the front surface side of the semiconductor device, the laser beam is interrupted by wide power-supply lines or the like; therefore, the analysis from the back side is indispensable. On the other hand, where the laser beam is injected from the back side of the semiconductor device, the laser beam can reach only the fourth layer at best from the bottom. Therefore, when the failure observed image is an OBIRCH image, it is preferable to designate a layer within the reach of the laser beam, as a layer of an analysis object in extraction of a net passing in the analysis region.

The semiconductor failure analysis apparatus, failure analysis method, and failure analysis program according to the present invention are not limited to the above-described embodiments and configuration examples, but can be modified in various ways. For example, the equipotential trace for the candidate interconnection using the pattern data group was described as to the configuration wherein the equipotential trace is carried out while setting the search layer and the trace layer in the above example, but, without having to be limited to this method, the analysis may be carried out by always using all the layers as objects in the extraction and trace of the interconnection patterns, instead of the configuration wherein the search layer, trace layer, etc. are allowed to set.

The semiconductor failure analysis apparatus according to the above embodiment is a semiconductor failure analysis apparatus for analyzing a failure of a semiconductor device, comprising: (1) inspection information acquiring means for acquiring a failure observed image containing reaction information arising from a failure, acquired by conducting an inspection about the failure, as an observed image of the semiconductor device; (2) layout information acquiring means for acquiring layout information of the semiconductor device; and (3) failure analyzing means for analyzing the failure of the semiconductor device with reference to the failure observed image and the layout information; (4) wherein the failure analyzing means has region setting means for setting an analysis region in correspondence to the reaction information with reference to the failure observed image, and interconnection information analyzing means for performing an analysis of a failure in a plurality of interconnections included in a layout of the semiconductor device, with reference to the analysis region; (5) wherein the layout information contains interconnection information to describe a configuration of the plurality of interconnections in the semiconductor device by a pattern data group of interconnection patterns in respective layers in a layer structure of the semiconductor device; and (6) wherein the interconnection information analyzing means extracts an interconnection passing the analysis region out of the plurality of interconnections, as a candidate interconnection for a failure and, for extracting the candidate interconnection, the interconnection information analyzing means performs an equipotential trace of the interconnection patterns using the pattern data group, thereby extracting the candidate interconnection.

The semiconductor failure analysis method is a semiconductor failure analysis method of analyzing a failure of a semiconductor device, comprising: (1) an inspection information acquiring step of acquiring a failure observation image containing reaction information caused by a failure, acquired by conducting an inspection about the failure, as an observed image of the semiconductor device; (2) a layout information acquiring step of acquiring layout information of the semiconductor device; and (3) a failure analyzing step of analyzing the failure of the semiconductor device with reference to the failure observed image and the layout information; (4) wherein the failure analyzing step comprises a region setting step for setting an analysis region in correspondence to the reaction information with reference to the failure observed image, and an interconnection information analyzing step of performing an analysis of a failure in a plurality of interconnections included in a layout of the semiconductor device, with reference to the analysis region; (5) wherein the layout information contains interconnection information to describe a configuration of the plurality of interconnections in the semiconductor device by a pattern data group of interconnection patterns in respective layers in a layer structure of the semiconductor device; and (6) wherein the interconnection information analyzing step comprises extracting an interconnection passing the analysis region out of the plurality of interconnections, as a candidate interconnection for a failure and, for extracting the candidate interconnection, the interconnection information analyzing step comprises performing an equipotential trace of the interconnection patterns using the pattern data group, thereby extracting the candidate interconnection.

The semiconductor failure analysis program is a program for letting a computer execute a semiconductor failure analysis of analyzing a failure of a semiconductor device, the program letting the computer execute: (1) an inspection information acquiring process of acquiring a failure observed image containing reaction information arising from a failure, acquired by conducting an inspection about the failure, as an observed image of the semiconductor device; (2) a layout information acquiring process of acquiring layout information of the semiconductor device; and (3) a failure analyzing process of analyzing the failure of the semiconductor device with reference to the failure observed image and the layout information; (4) wherein the failure analyzing process comprises a region setting process for setting an analysis region in correspondence to the reaction information with reference to the failure observed image, and an interconnection information analyzing process of performing an analysis of a failure in a plurality of interconnections included in a layout of the semiconductor device, with reference to the analysis region; (5) wherein the layout information contains interconnection information to describe a configuration of the plurality of interconnections in the semiconductor device by a pattern data group of interconnection patterns in respective layers in a layer structure of the semiconductor device; and (6) wherein the interconnection information analyzing process comprises extracting an interconnection passing the analysis region out of the plurality of interconnections, as a candidate interconnection for a failure and, for extracting the candidate interconnection, the interconnection information analyzing process comprises performing an equipotential trace of the interconnection patterns using the pattern data group, thereby extracting the candidate interconnection.

Concerning the extraction of the candidate interconnection, the failure analysis apparatus is preferably configured as follows; among the plurality of layers in the semiconductor device, the interconnection information analyzing means sets a search layer used in extraction of the candidate interconnection passing the analysis region, and a trace layer used in the equipotential trace of the interconnection patterns. Similarly, the failure analysis method is preferably configured as follows; among the plurality of layers in the semiconductor device, the interconnection information analyzing step comprises setting a search layer used in extraction of the candidate interconnection passing the analysis region, and a trace layer used in the equipotential trace of the interconnection patterns. Similarly, the failure analysis program is preferably configured as follows; among the plurality of layers in the semiconductor device, the interconnection information analyzing process comprises setting a search layer used in extraction of the candidate interconnection passing the analysis region, and a trace layer used in the equipotential trace of the interconnection patterns.

When the search layer and the trace layer each are set according to the specific layer structure and device structure among the plurality of layers constituting the semiconductor device as described above, it is feasible to suitably execute the extraction of the candidate interconnection by the equipotential trace of the interconnection patterns.

Furthermore, concerning the extraction of the candidate interconnection, the failure analysis apparatus is preferably configured as follows; among the plurality of layers in the semiconductor device, the interconnection information analyzing means sets a break layer where the equipotential trace of the interconnection patterns ends. Similarly, the failure analysis method is preferably configured as follows; among the plurality of layers in the semiconductor device, the interconnection information analyzing step comprises setting a break layer where the equipotential trace of the interconnection patterns ends. Similarly, the failure analysis program is preferably configured as follows; among the plurality of layers in the semiconductor device, the interconnection information analyzing process comprises setting a break layer where the equipotential trace of the interconnection patterns ends.

When the break layer to terminate the equipotential trace is set among the plurality of layers constituting the semiconductor device as described above, it becomes feasible to execute a variety of failure analyses, e.g., designating as a break layer a layer to which gates of transistors are connected, and separately detecting a light-emitting transistor.

In the configuration permitting the setting of the break layer as described above, the failure analysis apparatus may be arranged as follows; the interconnection information analyzing means has a first mode of extracting only an interconnection terminated in the break layer, and a second mode of extracting an interconnection without reference to the break layer, as trace modes in the equipotential trace of the interconnection patterns.

Similarly, the failure analysis method may be configured as follows; the interconnection information analyzing step has a first mode of extracting only an interconnection terminated in the break layer, and a second mode of extracting an interconnection without reference to the break layer, as trace modes in the equipotential trace of the interconnection patterns.

Similarly, the failure analysis program may be configured as follows; the interconnection information analyzing process has a first mode of extracting only an interconnection terminated in the break layer, and a second mode of extracting an interconnection without reference to the break layer, as trace modes in the equipotential trace of the interconnection patterns.

This configuration enables switching between the trace modes of the interconnection patterns, for example, according to an image acquisition condition for the failure observed image used in the failure analysis or according to a situation of occurrence of reaction in the semiconductor device. This improves the certainty of the failure analysis of the semiconductor device using the failure observed image.

Furthermore, the failure analysis apparatus is preferably configured as follows; for the equipotential trace of the interconnection patterns, the interconnection information analyzing means sets a maximum number of extracted patterns to limit a number of the interconnection patterns to be extracted. Similarly, the failure analysis method is preferably configured as follows; for the equipotential trace of the interconnection patterns, the interconnection information analyzing step comprises setting a maximum number of extracted patterns to limit a number of the interconnection patterns to be extracted. Similarly, the failure analysis program is preferably configured as follows; for the equipotential trace of the interconnection patterns, the interconnection information analyzing process comprises setting a maximum number of extracted patterns to limit a number of the interconnection patterns to be extracted. This makes it feasible to suitably execute the extraction of the candidate interconnection by the equipotential trace of the interconnection patterns using the interconnection information such as the GDS data.

The failure analysis apparatus is preferably configured as follows; the region setting means sets the analysis region in a layout coordinate system corresponding to the layout of the semiconductor device. Similarly, the failure analysis method is preferably configured as follows; the region setting step comprises setting the analysis region in a layout coordinate system corresponding to the layout of the semiconductor device. Similarly, the failure analysis program is preferably configured as follows; the region setting process comprises setting the analysis region in a layout coordinate system corresponding to the layout of the semiconductor device.

When the analysis region extracted and set from the failure observed image is expressed in the layout coordinate system instead of the coordinate system on the image as described above, it becomes feasible to efficiently execute the extraction of the candidate interconnection from the plurality of interconnections included in the layout of the semiconductor device, with reference to the analysis region set in the layout coordinate system.

The present invention is applicable as the semiconductor failure analysis apparatus, failure analysis method, and failure analysis program capable of securely and efficiently performing the analysis of the failure of the semiconductor device using the failure observed image.

What is claimed is:

1. A semiconductor failure analysis apparatus for analyzing a failure of a semiconductor device, comprising:
   inspection information acquiring means for acquiring a failure observed image containing reaction information arising from a failure, acquired by conducting an inspection about the failure, as an observed image of the semiconductor device;
   layout information acquiring means for acquiring layout information of the semiconductor device; and
   failure analyzing means for analyzing the failure of the semiconductor device with reference to the failure observed image and the layout information;

wherein the failure analyzing means has region setting means for setting an analysis region in correspondence to the reaction information with reference to the failure observed image, and interconnection information analyzing means for performing an analysis of a failure in a plurality of interconnections included in a layout of the semiconductor device, with reference to the analysis region;

wherein the layout information contains interconnection information to describe a configuration of the plurality of interconnections in the semiconductor device by a pattern data group of interconnection patterns in respective layers in a layer structure of the semiconductor device and connection relations between the interconnection patterns in the layers; and wherein the interconnection information analyzing means extracts an interconnection passing the analysis region out of the plurality of interconnections, as a candidate interconnection for a failure and, for extracting the candidate interconnection, the interconnection information analyzing means performs an equipotential trace of the interconnection patterns using the pattern data group, thereby extracting the candidate interconnection, and in extraction of the candidate interconnection by using the equipotential trace of the interconnection patterns, the interconnection information analyzing means extracts an interconnection pattern within the analysis region as an interconnection pattern portion with a possibility of forming the candidate interconnection, and the equipotential trace of the interconnection patterns is carried out across the plurality of layers from a start point of the extracted interconnection pattern with reference to the connection relations between the interconnection patterns in the layers, wherein at least the failure analyzing means is implemented by a computing device or a processor.

2. The failure analysis apparatus according to claim 1, wherein, among the plurality of layers in the semiconductor device, the interconnection information analyzing means sets a search layer used in extraction of the interconnection pattern within the analysis region with a possibility of forming the candidate interconnection passing the analysis region, and a trace layer used in the equipotential trace of the interconnection patterns.

3. The failure analysis apparatus according to claim 1, wherein, among the plurality of layers in the semiconductor device, the interconnection information analyzing means sets a break layer where the equipotential trace of the interconnection patterns ends.

4. The failure analysis apparatus according to claim 3, wherein the interconnection information analyzing means has a first mode of extracting only an interconnection terminated in the break layer, and a second mode of extracting an interconnection without reference to the break layer, as trace modes in the equipotential trace of the interconnection patterns.

5. The failure analysis apparatus according to claim 1, wherein, for the equipotential trace of the interconnection patterns, the interconnection information analyzing means sets a maximum number of extracted patterns to limit a number of the interconnection patterns to be extracted.

6. The failure analysis apparatus according to claim 1, wherein the region setting means sets the analysis region in a layout coordinate system corresponding to the layout of the semiconductor device.

7. A semiconductor failure analysis method of analyzing a failure of a semiconductor device, comprising:

an inspection information acquiring step of acquiring a failure observed image containing reaction information arising from a failure, acquired by conducting an inspection about the failure, as an observed image of the semiconductor device;

a layout information acquiring step of acquiring layout information of the semiconductor device; and a failure analyzing step of analyzing the failure of the semiconductor device with reference to the failure observed image and the layout information;

wherein the failure analyzing step comprises a region setting step for setting an analysis region in correspondence to the reaction information with reference to the failure observed image, and an interconnection information analyzing step of performing an analysis of a failure in a plurality of interconnections included in a layout of the semiconductor device, with reference to the analysis region;

wherein the layout information contains interconnection information to describe a configuration of the plurality of interconnections in the semiconductor device by a pattern data group of interconnection patterns in respective layers in a layer structure of the semiconductor device and connection relations between the interconnection patterns in the layers; and wherein the interconnection information analyzing step comprises extracting an interconnection passing the analysis region out of the plurality of interconnections, as a candidate interconnection for a failure and, for extracting the candidate interconnection, the interconnection information analyzing step comprises performing an equipotential trace of the interconnection patterns using the pattern data group, thereby extracting the candidate interconnection, and in extraction of the candidate interconnection by using the equipotential trace of the interconnection patterns, the interconnection information analyzing step extracts an interconnection pattern within the analysis region as an interconnection pattern portion with a possibility of forming the candidate interconnection, and the equipotential trace of the interconnection patterns is carried out across the plurality of layers from a start point of the extracted interconnection pattern with reference to the connection relations between the interconnection patterns in the layers, wherein at least the failure analyzing step is performed by a semiconductor failure analysis apparatus.

8. The failure analysis method according to claim 7, wherein, among the plurality of layers in the semiconductor device, the interconnection information analyzing step comprises setting a search layer used in extraction of the interconnection pattern within the analysis region with a possibility of forming the candidate interconnection passing the analysis region, and a trace layer used in the equipotential trace of the interconnection patterns.

9. The failure analysis method according to claim 7, wherein, among the plurality of layers in the semiconductor device, the interconnection information analyzing step comprises setting a break layer where the equipotential trace of the interconnection patterns ends.

10. The failure analysis method according to claim 9, wherein the interconnection information analyzing step has a first mode of extracting only an interconnection terminated in the break layer, and a second mode of extracting an interconnection without reference to the break layer, as trace modes in the equipotential trace of the interconnection patterns.

11. The failure analysis method according to claim 7, wherein, for the equipotential trace of the interconnection patterns, the interconnection information analyzing step comprises setting a maximum number of extracted patterns to limit a number of the interconnection patterns to be extracted.

12. The failure analysis method according to claim 7, wherein the region setting step comprises setting the analysis region in a layout coordinate system corresponding to the layout of the semiconductor device.

13. A non-transitory computer-readable storage medium having embodied thereon a program which causes a computer to execute a semiconductor failure analysis of analyzing a failure of a semiconductor device,
the program causing the computer to execute:
an inspection information acquiring process of acquiring a failure observed image containing reaction information arising from a failure, acquired by conducting an inspection about the failure, as an observed image of the semiconductor device;
a layout information acquiring process of acquiring layout information of the semiconductor device; and
a failure analyzing process of analyzing the failure of the semiconductor device with reference to the failure observed image and the layout information;
wherein the failure analyzing process comprises a region setting process for setting an analysis region in correspondence to the reaction information with reference to the failure observed image, and an interconnection information analyzing process of performing an analysis of a failure in a plurality of interconnections included in a layout of the semiconductor device, with reference to the analysis region;
wherein the layout information contains interconnection information to describe a configuration of the plurality of interconnections in the semiconductor device by a pattern data group of interconnection patterns in respective layers in a layer structure of the semiconductor device and connection relations between the interconnection patterns in the layers; and
wherein the interconnection information analyzing process comprises extracting an interconnection passing the analysis region out of the plurality of interconnections, as a candidate interconnection for a failure and, for extracting the candidate interconnection, the interconnection information analyzing process comprises performing an equipotential trace of the interconnection patterns using the pattern data group, thereby extracting the candidate interconnection, and
in extraction of the candidate interconnection by using the equipotential trace of the interconnection patterns, the interconnection information analyzing process extracts an interconnection pattern within the analysis region as an interconnection pattern portion with a possibility of forming the candidate interconnection, and the equipotential trace of the interconnection patterns is carried out across the plurality of layers from a start point of the extracted interconnection pattern with reference to the connection relations between the interconnection patterns in the layers.

14. The failure analysis program according to claim 13, wherein, among the plurality of layers in the semiconductor device, the interconnection information analyzing process comprises setting a search layer used in extraction of the interconnection pattern within the analysis region with a possibility of forming the candidate interconnection passing the analysis region, and a trace layer used in the equipotential trace of the interconnection patterns.

15. The failure analysis program according to claim 13, wherein, among the plurality of layers in the semiconductor device, the interconnection information analyzing process comprises setting a break layer where the equipotential trace of the interconnection patterns ends.

16. The failure analysis program according to claim 15, wherein the interconnection information analyzing process has a first mode of extracting only an interconnection terminated in the break layer, and a second mode of extracting an interconnection without reference to the break layer, as trace modes in the equipotential trace of the interconnection patterns.

17. The failure analysis program according to claim 13, wherein, for the equipotential trace of the interconnection patterns, the interconnection information analyzing process comprises setting a maximum number of extracted patterns to limit a number of the interconnection patterns to be extracted.

18. The failure analysis program according to claim 13, wherein the region setting process comprises setting the analysis region in a layout coordinate system corresponding to the layout of the semiconductor device.

* * * * *